US007024369B1

(12) United States Patent
Brown et al.

(10) Patent No.: US 7,024,369 B1
(45) Date of Patent: Apr. 4, 2006

(54) BALANCING THE COMPREHENSIVE HEALTH OF A USER

(75) Inventors: Michael Wayne Brown, Georgetown, TX (US); Kelvin Roderick Lawrence, Round Rock, TX (US); Michael A. Paolini, Round Rock, TX (US)

(73) Assignee: International Business Machines Corporation, Armonk, NY (US)

( * ) Notice: Subject to any disclaimer, the term of this patent is extended or adjusted under 35 U.S.C. 154(b) by 919 days.

(21) Appl. No.: 09/583,943

(22) Filed: May 31, 2000

(51) Int. Cl.
*G06F 17/60* (2006.01)
(52) U.S. Cl. ............................... 705/2; 705/3; 600/513; 600/300
(58) Field of Classification Search .................... 705/2, 705/3, 36, 44, 7; 600/300, 513, 301, 3; 700/95; 345/837, 853; 706/45
See application file for complete search history.

(56) References Cited

U.S. PATENT DOCUMENTS

| | | | | |
|---|---|---|---|---|
| 4,951,197 | A | | 8/1990 | Mellinger .................... 600/300 |
| 5,542,420 | A | | 8/1996 | Goldman et al. ........... 600/301 |
| 5,778,882 | A | * | 7/1998 | Raymond et al. ........... 600/513 |
| 5,890,128 | A | * | 3/1999 | Diaz et al. ...................... 705/2 |
| 5,980,447 | A | * | 11/1999 | Trudeau ......................... 600/3 |
| 6,208,974 | B1 | * | 3/2001 | Campbell et al. .............. 705/3 |

FOREIGN PATENT DOCUMENTS

EP        342859 A   *  11/1989

OTHER PUBLICATIONS

Gulf Goans' Mailing List Newsletter, GOA-World—Weekend Post Newsletter—vol. XIII—Nov. 25, 1998. [Retrieved on Dec. 9, 2002]. Retrieved from Internet; URL: <http://www.goa-world.net/gulf_goans/nov31.htm>.*
Lordan, Craig. Notes.Net Mail Filtering. 1999.[Retrieved on Dec. 9, 2002]. Retrieved from Internet; URL: > http://www-10.lotus.com/ldd/today.nsf/62f62847467a8f78052568a80055b380/4541559cb15c46e285256815007b107d/$FILE/mailrule.pdf>.*
Department of Defense Population Health Improvement Plan and Guide, DoD TRICARE Management Activity. Dec. 2001. [Retrieved on Dec. 8, 2002], Retrieved from Internet. URL:< http://www.tricare.osd.mil/mhsophsc/DoD$_{13}$PHI_Plan_Guide.pdf>.*

* cited by examiner

*Primary Examiner*—Joseph Thomas
*Assistant Examiner*—Natalie A. Pass
(74) *Attorney, Agent, or Firm*—Marilyn S. Dawkins; Dillon & Yudell LLP

(57) ABSTRACT

A current health profile for a user is monitored at a personal health monitoring system. The current health profile includes multiple monitored physical parameters and multiple monitored environmental parameters. Multiple actions for selection by the user are received at the personal health monitoring system. The multiple actions are prioritized according to the current health profile and designated allowances for the user at the personal health monitoring system, such that the personal health monitoring system aids the user in selecting from among the multiple actions in order to balance the comprehensive health of the user. Multiple tasks for scheduling in a user's electronic schedule are scheduled according to the current health profile and designated allowances for the user at the personal health monitoring system.

65 Claims, 13 Drawing Sheets

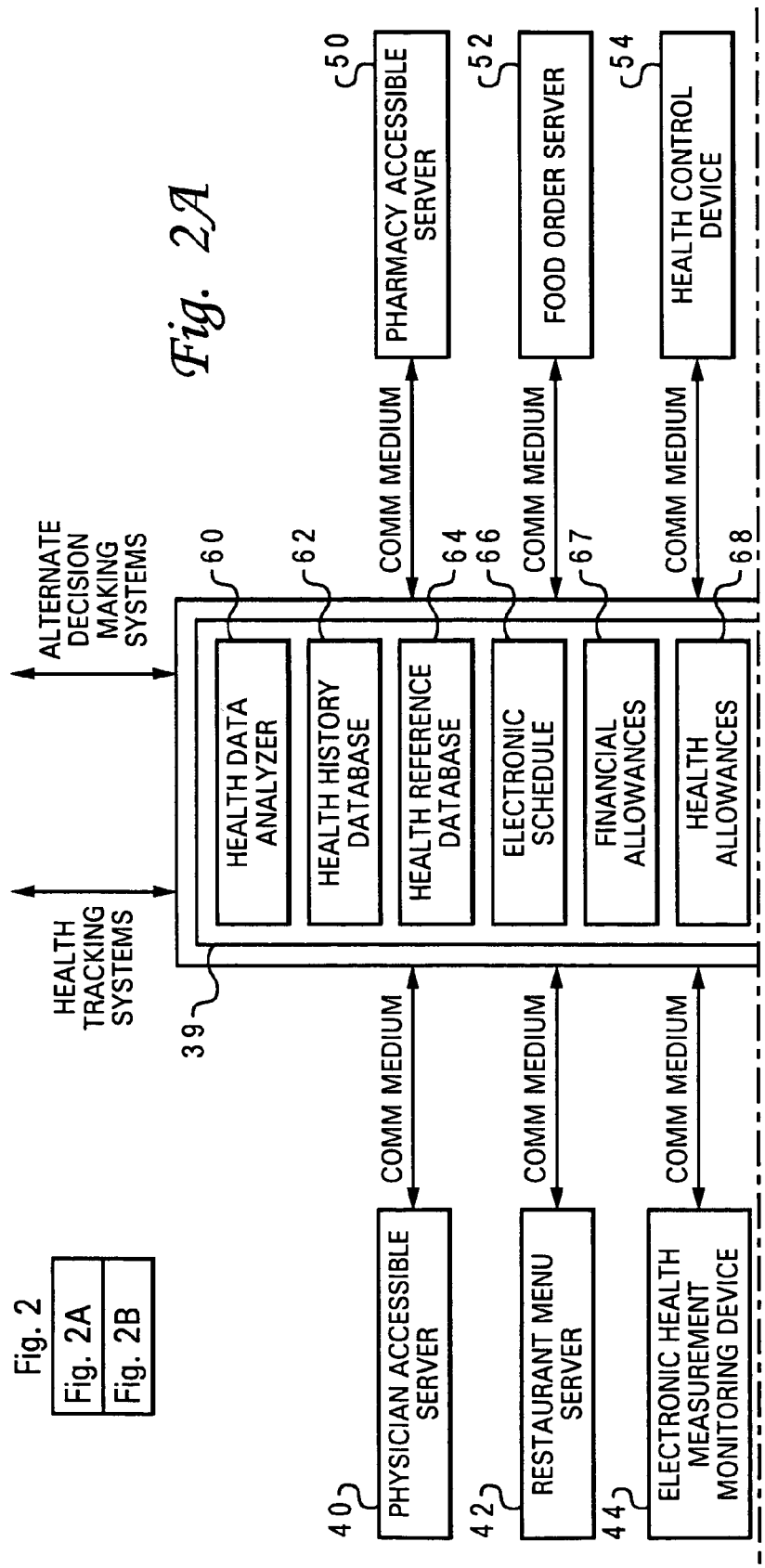

BALANCING THE COMPREHENSIVE HEALTH OF A USER

CROSS-REFERENCE TO RELATED APPLICATIONS

The present application is related to the following co-pending applications, which are filed on even date herewith and incorporated herein by reference:

(1) U.S. patent application Ser. No. 09/583,942; and
(2) U.S. patent application Ser. No. 09/583,941.

BACKGROUND OF THE INVENTION

1. Technical Field

The present invention relates in general to health management and in particular to a method, system, and program for balancing the comprehensive health of a user. Still more particularly, the present invention relates to a method, system, and program for recommending actions to a user and scheduling tasks for the user in a manner as to balance the comprehensive health of the user.

2. Description of the Related Art

From visiting doctor's offices, to attending health clubs, to shopping at health food markets, it is well known that people struggle to find ways to maintain and achieve diverse health goals and levels. When feeling ill, or anticipating illness, such as from traveling or allergies, people request medication from their doctors to balance their health. Some people attempt to lose weight, while others attempt to gain weight or strength by attending a health club. Others' goals include attempts to rehabilitate from injuries, illness or surgery with a physical therapist. And yet, still others attempt to maintain certain nutritional or philosophical goals, such as not consuming animal products.

As is well known, multiple agencies, groups and professional people provide suggestions, guidelines, consulting and analysis in order to provide attainable steps towards a person's health goals. For example, the government provides a chart of recommended daily consumption. Organizations like Jenny Craig® provide people with a list of menus and food intake options. In addition, such organizations typically provide counseling and cooking techniques. Prescription medication companies provide advertising and free consultations to see whether their medication can alleviate pain or aid in meeting a health goal. Physical therapists prescribe particular exercises to facilitate rehabilitation. Gym trainers determine a strength training program that will help a person gain strength according to their health goals. Even some grocery stores provide consultants who direct a user to purchase certain types of products depending on their health goals.

Many health plans require a user to record information such as caloric or liquid intake and exercise and provide the recorded information to a consultant, who then determines whether the user is staying on track with health goals. However, manually recording daily calorie consumption, daily exercise, environmental factors and such can be time consuming and relies on the person to be efficient in personally tracking data. While checking in with a trained professional who has provided a fitness and/or eating plan is important and can aid a person in monitoring and meeting his/her goals, this system is not entirely efficient. Moreover, most programs do not easily accommodate for shifts in a person's schedule or in the environment. For example, most programs do not shift the amount of water recommended in a person's diet after they have hiked for 2 hours in 90 degree heat.

In addition, current health plans can not provide for making real time recommendations to a user about what actions would best meet the health goals of the user. For example, most health plans do not provide real time recommendations for selections from a particular food menu at a particular restaurant according to what a user has already eaten that day, how much exercise the user has done, what environment the user has been exposed to, what medications the user is taking, how much time the user has to eat, and how much money the user can spend on the meal.

Moreover, current health plans do not provide for making recommendations for scheduling multiple diverse tasks for a user in order to best meet the health goals of the user. Some health plans may recommend certain exercise times, however, most people balance many different responsibilities during the day including children, work, eating and exercising and current health plans do not adjust for the daily changes that may occur in a user's schedule because of all these factors.

Furthermore, current health plans only look at what a user eats and how much they exercise and do not attempt to balance all the factors that play into a user's overall well-being, herein termed comprehensive health. For example, how a user spends time, spends financial resources and treats his/her body all factor into a user's comprehensive health. In particular, current health plans do not provide for making scheduling recommendations for the multiple diverse tasks that a user needs to perform each day in order to balance the user's comprehensive health.

As the tide is turning towards a paperless world, computers are becoming more prevalent in order to replace many functions previously performed utilizing paper and people. In particular, computing devices, such as personal digital assistants, laptop computers and cellular/digital telephones are becoming more commonplace as a personal, portable computer system. In addition, personal storage devices that include limited processing power, such as smart cards, are becoming more prevalent as an easily transportable and secure way to transfer data. Moreover, the advent of the network, and particular the Internet, makes it possible for a user to access data stored at a particular location in the network from any other computer system with access to that network.

However, computers, smart cards and network systems have not yet been implemented in an efficient way as a personal health monitoring assistant to balance the comprehensive health of a user, including physical, mental and spiritual well-being. In view of the foregoing, it would be preferable to utilize a computing device such as a portable computer system, personal storage device, and/or network system to received monitored physical and environmental parameters of a user's health and recommend actions to a user in an attempt to balance a user's comprehensive health according to time, financial, and health allowances designated by the user, the personal health monitoring system, or a health consultant. In addition, it would be preferably to utilize the computing device to schedule tasks for a user in an attempt to balance the user's comprehensive health according to time, financial, and health allowances.

SUMMARY OF THE INVENTION

In view of the foregoing, it is therefore an object of the present invention to provide improved health management.

It is another object of the present invention to provide an improved method, system, and program for balancing the comprehensive health of a user.

It is yet another object of the present invention to provide an improved method, system, and program for recommending actions to a user and scheduling tasks for the user in a manner as to balance the comprehensive health of the user.

In accordance with the present invention, a current health profile for a user is monitored at a personal health monitoring system. The current health profile includes multiple monitored physical parameters and multiple monitored environmental parameters. Multiple actions for selection by the user are received at the personal health monitoring system. The multiple actions are prioritized according to the current health profile and designated allowances for the user at the personal health monitoring system, such that the personal health monitoring system aids the user in selecting from among the multiple actions in order to balance the comprehensive health of the user.

In addition, multiple tasks for scheduling in a user's electronic schedule are received at the personal health monitoring system. The multiple tasks are scheduled according to the current health profile and designated allowances for the user at the personal health monitoring system, such that the personal health monitoring system aids the user in scheduling tasks in order to balance the comprehensive health of the user.

All objects, features, and advantages of the present invention will become apparent in the following detailed written description.

BRIEF DESCRIPTION OF THE DRAWINGS

The novel features believed characteristic of the invention are set forth in the appended claims. The invention itself, however, as well as a preferred mode of use, further objects, and advantages thereof, will best be understood by reference to the following detailed description of an illustrative embodiment when read in conjunction with the accompanying drawings, wherein:

DETAILED DESCRIPTION OF ILLUSTRATIVE EMBODIMENT

The present invention may be executed in a variety of systems, including a variety of computing systems and electronic devices under a number of different operating systems. In a preferred embodiment of the present invention, the computer system is a portable computing system such as a notebook computer, a palmtop computer, a personal digital assistant, a telephone or other electronic computing system that may also incorporate communication features that provides for telephony, enhanced telephony, messaging and information services. However, the computer system may also be, for example, a desktop computer, a network computer, a midrange computer or a mainframe computer. Preferably, in order to enable at least one of these communication features, the computer system is able to be connected to a network, such as the Internet by either a wired link or wireless link. In addition, the computer system may be a stand-alone system or part of a network such as a local-area network (LAN) or a wide-area network (WAN). Therefore, in general, the present invention is preferably executed in a computer system that performs computing tasks such as manipulating data in storage that is accessible to the computer system. In addition, the computer system includes at least one output device and at least one input device.

Figure 1:
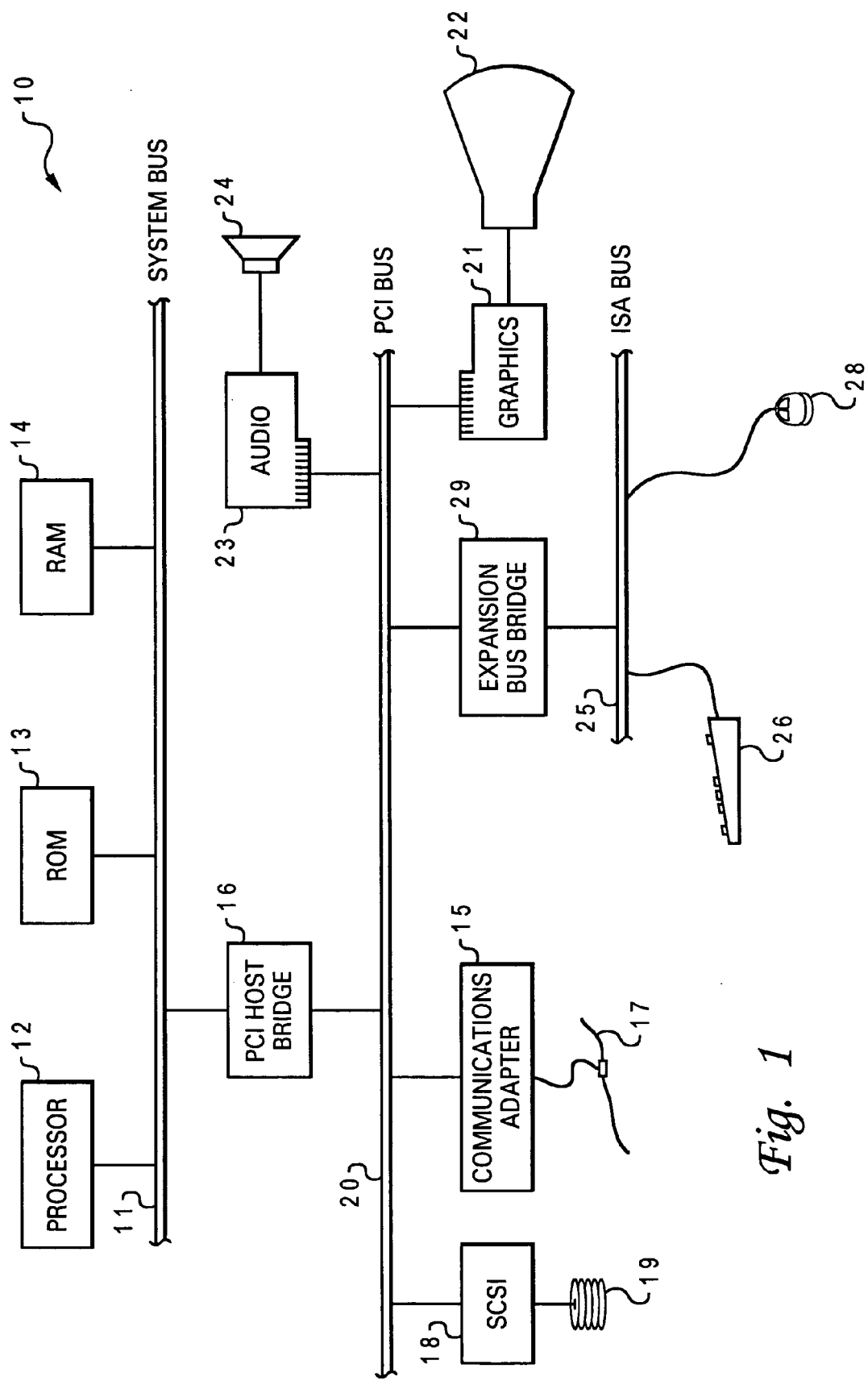
FIG. 1 depicts a block diagram of one embodiment of a computer system that may utilize the present invention.

Referring now to the drawings and in particular to FIG. 1, there is depicted a block diagram of one embodiment of a computer system that may utilize the present invention. As depicted, data processing system 10 includes at least one processor 12, which is coupled to system bus 11. Each processor 12 is a general-purpose processor, such as IBM's PowerPC™ processor that, during normal operation, processes data under the control of operating system and application software stored in random access memory (RAM) 14 and Read Only Memory (ROM) 13. The operating system preferably provides a graphical user interface (GUI) to the user. Application software contains instructions that when executed on processor 12 carry out the operations depicted in the flowcharts of FIGS. 3, 5, 6, 8, 12 and others described herein.

Processors 12 are coupled via system bus 11 and Peripheral Component Interconnect (PCI) host bridge 16 to PCI local bus 20. PCI host bridge 16 provides a low latency path through which processor 12 may directly access PCI devices mapped anywhere within bus memory and/or I/O address spaces. PCI host bridge 16 also provides a high bandwidth path for allowing PCI devices to directly access RAM 14.

PCI local bus 20 interconnects a number of devices for communication under the control of PCI controller 30. These devices include a Small Computer System Interface (SCSI) controller 18, which provides an interface to SCSI hard disk 19, and communication adapter(s) 15, which interface data processing system 10 to at least one data communication network 17 comprising wired and/or wireless network communication. In addition, an audio adapter 23 is attached to PCI local bus 20 for controlling audio output through speaker 24. A graphics adapter 21 is also attached to PCI local bus 20 for controlling visual output through display monitor 22. In alternate embodiments of the present invention, additional peripheral components may be added. For example, in alternate embodiments, a tactile display component may be provided.

PCI local bus 20 is further coupled to an Industry Standard Architecture (ISA) bus 25 by an expansion bus bridge 29. As shown, ISA bus 25 has an attached I/O (Input/Output) controller 34 that interfaces data processing system 10 to peripheral input devices such as a keyboard and mouse (not illustrated) and supports external communication via parallel, serial and universal serial bus (USB) ports 26, 27, and 28, respectively.

Figure 2B:
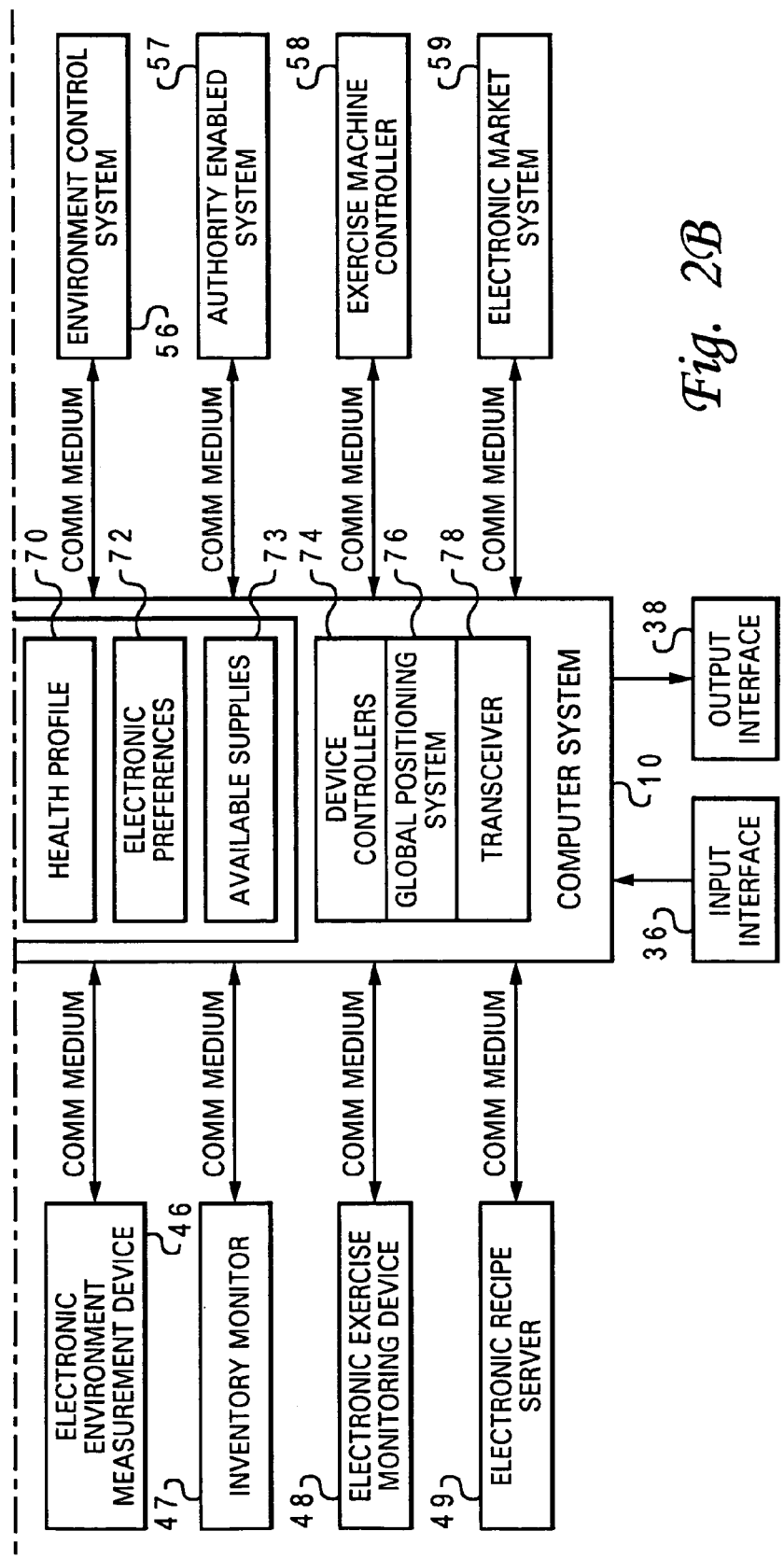
FIG. 2 illustrates a block diagram of one embodiment of a personal health monitoring and management system in accordance with the method, system and program of the present invention.

With reference now to FIG. 2, there is depicted a block diagram of one embodiment of a personal health monitoring and management system in accordance with the method, system and program of the present invention. It has been shown that there are many factors that are influential to a user's overall well-being, herein termed as balanced comprehensive health. Not only does what one eats and how much one exercises effect well-being, but what one is exposed to, what medications one is taking, how those medications are actually treating the body, how one manages their time and financial resources, and other factors that effect one's physical and mental health. Therefore, in balancing a user's comprehensive health, computer system 10 intends to take into account a multitude of factors that may influence a user's overall well being to balance physical wellness, mental wellness and spiritual wellness.

Personal Health Monitoring System

As illustrated and will be further described, computer system 10 functions as a personal health monitoring system that receives inputs from multiple physical and environmental parameter measurement devices, balances a user's comprehensive health in view of the monitored physical and environmental parameters, determines suitable actions for a user in balancing the user's comprehensive health, and transmits outputs to physical and environmental control devices to adjust physical and environmental parameters for a user.

In the present embodiment, a data storage medium 39 is coupled with computer system 10 that includes a health data analyzer application 60, a health history database 62, a health reference database 64, an electronic schedule 66, a financial allowances database 67, a health allowances database 68, a health profile 70, and an electronic preferences database 72. While in the present embodiment data storage medium 39 is depicted as internally accessible to computer system 10, in alternate embodiments data storage medium 39 may be externally or remotely accessible to computer system 10. For example, the data depicted as stored in data storage medium 39 may be distributed across more than one server system coupled to a network, such as the Internet. In addition, for example, the data depicted as stored in data storage medium 39 may be retrieved from a personal storage device, such as a smart card.

In the present application, the comprehensive health of an individual includes time, financial, and health allowances that are balanced by computer system 10. Health data analyzer application 60 functions to manage the comprehensive health of a particular user at computer system 10 in response to multiple diverse physical and environmental parameters received at computer system 10.

In addition, health data analyzer application 60 recommends actions for a user from multiple diverse selectable actions received at computer system 10 in order to balance the comprehensive health of a user. In particular, health data analyzer application 60 prioritizes selectable actions in order to aid the user in selections and may adjust prioritization of selectable actions as the user makes selections. For example, health data analyzer application 60 may prioritize the contents of an electronic food menu. As the user makes selections from the electronic food menu, prioritization may be adjusted in order to compensate for selections being made.

Moreover, health data analyzer application 60 is enabled to determine control signals for transmission to multiple diverse physical and environmental health control systems to adjust a particular physical or environmental health parameter. Furthermore, health data analyzer application 60 may perform additional analysis functions, as will be further described herein.

Computer system 10 is enabled to communicate, via a communication medium, to multiple diverse input and output devices that will be further described herein. The communication medium may comprise a wired or wireless data link. In addition, the communication medium may comprise a network, such as the Internet, or a direct data link. In a wired embodiment of the communication medium, for example, multiple systems are connected to computer system 10 via parallel, serial, or USB ports, or the communication adapter as depicted in FIG. 1. In a wireless embodiment of the communication medium, multiple systems are wirelessly connected to computer system 10 via infrared, radio frequency (RF), cellular and other wireless transmissions which are detected by computer system 10.

Security filters and hooks may be applied to the communication medium at multiple points. Preferably, computer system 10 includes security filters for all input to and output from computer system 10. In addition, input devices to and output devices from computer system 10 may include security filters.

Security filters may limit types of data input/output, encrypt and decrypt data input/output, and require authentication and authorization to access data. In particular, security filters applied to data output from computer system 10 may filter data according to criteria including, but not limited to, the type of device being transmitted to, the universal identifier of the device being transmitted to, the type of data being transmitted, and other criteria that may be set by the user or by an authority to the user.

Data exchange across the communication medium is advantageously performed in at least one of multiple available data transmission protocols and is preferably supported by a common data structure format, such as the extensible mark-up language (XML) data structure format.

Data transmission protocols may include, but are not limited to, Transmission Control Protocol (TCP), Internet Protocol (IP), Hypertext Transfer Protocol (HTTP), and Bluetooth. In addition, data may be transmitted in a secure manner via encryption or by technologies, such as secure socket layer (SSL) or virtual private networks (VPN).

In addition, preferably at least one input interface 36 and at least one output interface 38 are coupled to computer system 10 in accordance with the present invention. Examples of input interface 36 may include, but are not limited to, a keyboard, a touch pad, a button pad, a voice recognition system, a stylus, a tactile-detectable interface, and others. Examples of output interface 38 may include, but are not limited to, a display monitor, a speaker, light emitting diodes (LEDs), vibration control, and others.

Health History

The comprehensive health of an individual also includes health history database 62. Health history database 62 preferably includes both health and non-health related parameters received at computer system 10 in association with a particular user. Health parameters may include physical and environmental parameters.

Physical parameters may include, but are not limited to including, monitored intake(i.e. food, liquid, and medication), bodily health measurements, and monitored exercise measurements. Environmental parameters may include, but are not limited to including, monitored temperatures, humidity, air content, air pressure, wind direction, light content, airborne disease, and geographical location. Non-health parameters may include, but are not limited to, usage of authority-enabled electronic devices, time parameters, financial parameters, actions received, tasks received, purchases made, and personal usage of computer system 10.

As will be further described, health history database 62 may be utilized for multiple types of analysis. In a first example, health history database 62 may be analyzed by health data analyzer 60 in order to determine factors that effect the health of a user over time and average health and non-health characteristics for a user. Factors that effect the health of a user and average health and non-health characteristics may be added to health profile 70 for a user. In addition, health data analyzer 60 may recommend to a user to adjust time, financial, or health allowances according to patterns and averages detected in analyzing health history database 62. Moreover, health data analyzer 60 may adjust electronic preferences database 72 according to patterns and averages detected in types of purchases made and actions selected by a user.

In addition, health history database 62 may be transmitted with additional data to alternate decision making systems. As will be further described, alternate decision making systems may include predetermined conditional analysis criteria for analyzing health history database 62 in order to detect factors that effect the health of the user and average health and non-health characteristics of the user. In addition, alternate decision making systems may make the contents of health history database 62 accessible to others, such as a physician, parent or employer who analyze health history database 62 according to selected criteria. A cluster of alternate decision making systems may incorporate both conditional analysis criteria and user selected analysis criteria for analysis of health history database 62. In particular, the cluster of alternate decision making systems may implement a hierarchical decision tree.

In response to analysis of health history database 62 performed at an alternate decision making system, recommendations and/or restrictions for adjustment to time, financial or health allowances may be transmitted from the alternate decision making system to computer system 10. For example, in analyzing a heath history database of a user that has high blood pressure over an extended period of time, a doctor analyzing the health history database may transmit a recommendation to the user's computer system for a particular diet and exercise that would require adjustment to time and health allowances for the user. In the same example, if the user does not make actual adjustments to diet and exercise and the high blood pressure continues, the doctor may transmit restrictions to time and health allowances that require the user to adhere to a particular diet and exercise regiment.

Health history database 62 may also be exported to alternate systems that perform analysis on multiple health history databases from multiple users to detect common health effecting factors among a control group of users. As will be further described, multiple types of groups may benefit from access to multiple health history databases from multiple users including, but not limited to, the American Medical Association(AMA), the Food and Drug Administration(FDA), drug researchers, employers, health insurance providers, and businesses.

Health References

Health reference database 64 provides multiple types of health and non-health related data that may be referenced by health data analyzer 60 in performing analysis. In particular, health reference database 64 may include reference data corresponding to physical and environmental parameters, including recommendations for responding to particular physical and environmental parameters. In addition, health reference database 64 may include recommended diets, exercise regiments, bodily health levels, and environmental exposure that may be adjusted by health data analyzer 60 according to the comprehensive health of a particular user. Moreover, health reference database 64 may include additional data associated with recommended manufacturers, wholesalers, and others that may be utilized by health data analyzer 60 in determining where and what to purchase.

Scheduling

Electronic schedule 66 preferably includes the time parameters for a user in the form of scheduled tasks to be performed. A user may designate multiple levels of priority for tasks to be scheduled in electronic schedule 66 and may designate time allowances for multiple types of tasks. As depicted in Table 1, time allowances are designated for multiple types of tasks. In the present example, work and Child A's athletic events take priority over dinner meals and exercise. In addition, in the present example, a minimum and maximum amount of daily time for dinner meals is designated, while for the other types of tasks a minimum and maximum amount of weekly time is designated.

TABLE 1

| Designated Time Allowances | | |
| --- | --- | --- |
| Type of Task | Task Priority | Min/Max Time Allowance |
| Dinner Meal | 3 | 15 min/1 hour (day) |
| Work | 2 | 35 hours/50 hours (week) |
| Child A's athletic events | 2 | 15 min/3 hours (week) |
| Exercise | 3 | 2 hours/8 hours (week) |

Health data analyzer application 60 advantageously determines what tasks to schedule, when to schedule tasks and recommends adjustments to scheduling when needed according to the priority assigned to tasks and time allowances. In particular, in scheduling tasks, health data analyzer application 60 preferably attempts to balance the comprehensive health of the user and thus considers time allowances, financial allowances, health allowances and a health profile 70, in addition to currently detected physical and environmental parameters and priority associated with the task.

When tasks with the same priority conflict for a scheduling time, health data analyzer application 60 attempts to reschedule one of the tasks and/or allow the user to select one of the tasks according to recommendations made by health data analyzer application 60. For example, if a conflict arose between child A's athletic event schedule and work, then health data analyzer application 60 would determine whether either the time for the athletic event or work could be rescheduled, and if not, allow the user to select between the two with a recommendation as to which task would best balance the user's comprehensive health.

As depicted in Table 1, a user may designate minimum and maximum times for tasks that should be performed routinely, such as daily, weekly, monthly or yearly. For example, in order to work at least 35 hours a week, a user may designate a task of being at work Tuesday through Saturday between the hours of 8 AM and 5 PM with a one hour lunch break. Additional work related tasks may be added to the schedule between the hours of 8 AM and 5 PM and tracked. In addition, non-work related tasks may be added to the schedule between the hours of 8 AM and 5 PM and the amount of time spent at non-work related tasks during designated work hours tracked so that the user and/or employer may monitor vacation, personal and sick time utilized.

In addition, as depicted in Table 1, a required weekly amount of exercise time may be designated by the user. Health data analyzer 66 might schedule tentative exercise times based on the user's schedule history and currently scheduled events in order to meet the requested amount of exercise time. Advantageously, the scheduled exercise tasks may be adjusted as additional tasks surface during the week. However, health data analyzer 66 may also recommend not adding additional tasks if sufficient time is not available to schedule the additional task and include the requested amount of exercise time while balancing the user's comprehensive health.

Computer system 10 may also receive recommended tasks from others. For example, a doctor may transmit a recommended exercise program that would be presented to the user in the form of exercise tasks to be added to electronic schedule 66. In another example, a co-worker may transmit a requested meeting time that would be compared with electronic schedule 66 by health data analyzer application 60 and recommendations made to the user according to whether or not the addition of the requested meeting time will maintain balance in the user's comprehensive health. For example, if the requested meeting time is outside of the user's normal work hours, then health data analyzer 60 may determine whether time, financial and health allowances will remain balanced if the after work meeting time is accepted. In particular, a priority may be associated with the requested meeting time that indicates possible financial implications if the user does not attend. In this case, the priority of the meeting time may take precedence over tasks of lower priority. For example, the user may have scheduled task for cooking dinner that evening that may be rescheduled for the user to pick-up dinner on the way home in order to utilize the preparation time for dinner to attend the meeting.

In addition, computer system 10 may receive conditional task requirements from others or the user. Prior to allowing a task to be scheduled or an action to be performed, health data analyzer application 60 determines whether or not any conditional task requirements are satisfied. In particular, conditional task requirements may be required to be true in order for access to an authority-enabled system 57 to be allowed. Authority-enabled system 57 and allowance to use of authority-enabled system 57 is described in U.S. patent application Ser. No. 09/560,393, herein incorporated by reference. For example, a parent may require in a conditional task requirement that a child participate in exercise for at least thirty minutes a day in order for time for access to television or video games to be allowed to be scheduled. In another example, a parent may require in a conditional task requirement that a child is located at school during scheduled school time in order to be allowed to access financial allowances 67 to make purchases that day.

Figure 3:
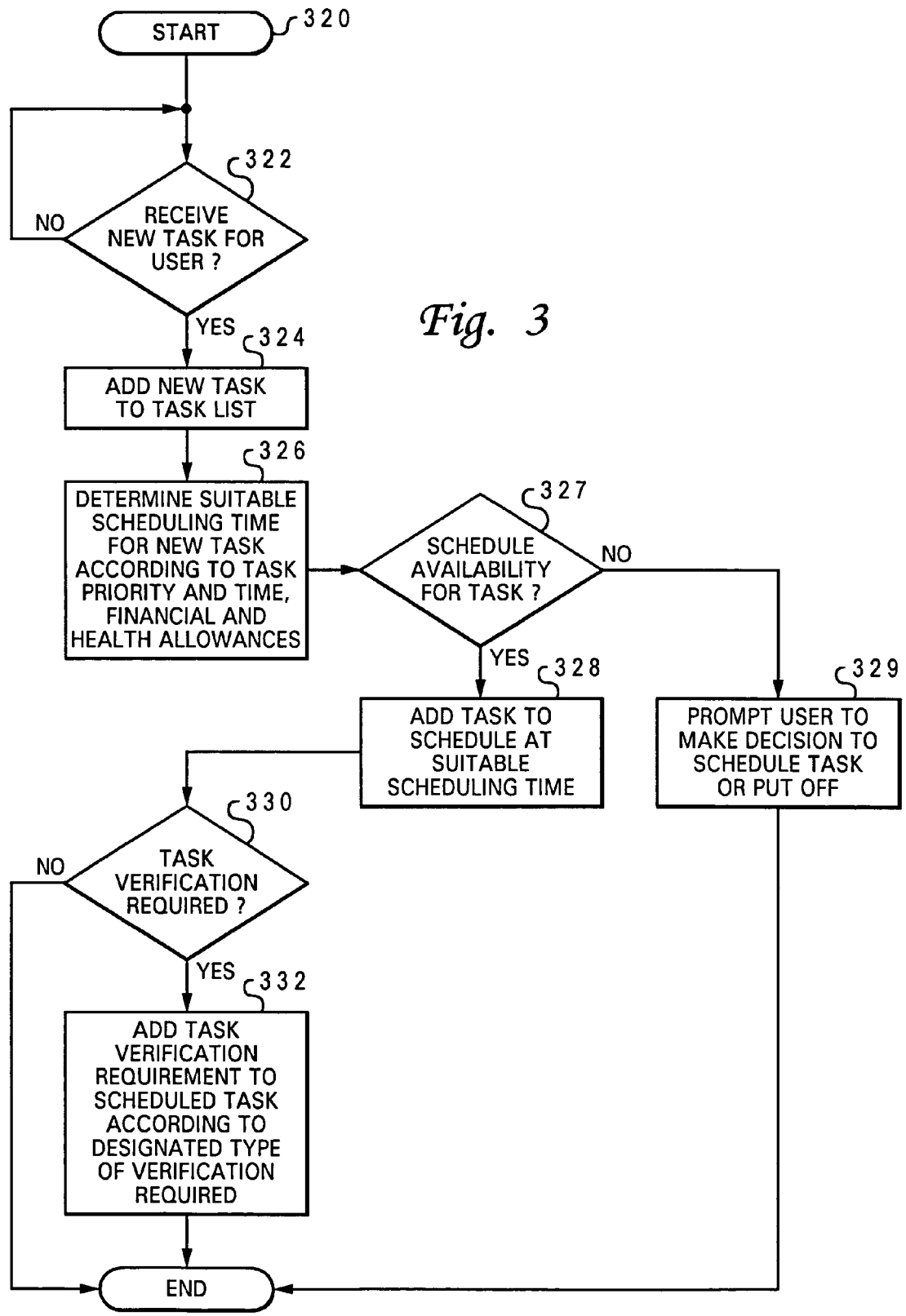
FIG. 3 depicts a high level logic flowchart of a process and program for scheduling tasks in accordance with the present invention.

With reference now to FIG. 3, there is depicted a high level logic flowchart of a process and program for scheduling tasks in accordance with the present invention. As illustrated, the process starts at block 320 and thereafter proceeds to block 322. Block 322 depicts a determination as to whether or not new tasks are received for the user. If a new task is not received, then the process iterates at block 322. If a new task is received, then the process passes to block 324.

Block 324 depicts adding the new task to the task list and updating the heath history database with the new task. Next, block 326 illustrates determining a suitable scheduling time for the new task according to the task priority, available time, financial, and health allowances. Thereafter, block 327 depicts a determination as to whether or not a suitable scheduling time is determined. If a suitable scheduling time is not determined, then the process passes to block 329. Block 329 illustrates prompting the user to make a manual scheduling decision; and the process ends. If a suitable scheduling time is determined, then the process passes to block 328.

Block 328 depicts adding the task to the schedule at the suitable scheduling time. In particular, in determining a suitable scheduling time, scheduled times of other tasks may be adjusted. Next, block 330 illustrates a determination as to whether or not task verification is required. If task verification is not required, then the process ends. If task verification is required, then the process passes to block 352. Block 352 depicts adding a task verification requirement to the scheduled task according to the type of verification required; and the process ends.

Finances

Financial allowances 68 include minimum and maximum financial budgeting limits for multiple allowance categories. For example, categories may include, but are not limited to including, meal allowances, snack allowances, grocery allowances, household allowances, medication allowances, healthcare allowances, travel allowances, donation allowances, gift allowances, clothing allowances, entertainment allowances, education allowances, and others. In addition, each category may include multiple subcategories to further define financial constraints. A user may determine categories and allowances for each category and subcategory in financial allowances 68. In addition, financial allowances 68 may utilize an existing budgetary application such as Quicken™ (Quicken is a trademark of Intuit, Inc.) where a user has designated allowances for each budget category.

Table 2 depicts an example of financial allowances 68 designated at computer system 10 for a particular user. As illustrated, a user has allotted $1.50 per day for an afternoon snack and has currently used $1.00. If the user does not use the remainder of the allowance during the afternoon, the remainder may be applied to savings, applied to an alternate allowance category, or added to the afternoon snack allowance for the next day.

In addition, the user has allotted $20.00 for perishable groceries and $30.00 for non-perishable groceries per week. The user only needed $25.00 for non-perishables for the week, so the $5.00 remainder may be applied to perishables for the week.

TABLE 2

Designated Financial Allowances

| Financial Category | Financial Subcategory | Financial Allowance | Current Financial Usage |
|---|---|---|---|
| Snack | Afternoon | $1.50 (day) | $1.00 |
| Grocery | Perishables | $20.00 (week) | $25.00 |
| Grocery | Non-perishable | $30.00 (week) | $25.00 |
| Medication | None | $60.00 (month) | $30.00 |

In addition, health data analyzer application 60 may determine categories and allowances for financial allowances 68 based on a user's current income, health history database 62, electronic schedule 66 and health allowances 70. In particular, health data analyzer application 60 attempts to determine allowances for the multiple categories of spending for a particular user in order to balance the comprehensive health of the particular user.

Advantageously, as depicted in Table 2, health data analyzer application 60 may adjust allowances assigned to categories according to changes in a user's needs. For example, in anticipation of vacation time for a user designated in electronic schedule 66, health data analyzer application 60 may decrease allowances in a category or several categories in order to redirect money for the user's vacation expenses. In addition, in correlation with a tax assistant application(not shown), health data analyzer application 60 may adjust allowances in several categories, such as donation allowances, in order to aid a user in maximizing deductions according to a user's income and changes in income due to changes such as unexpected growth or decline of investments. Moreover, in response to adjustments to health allowances 70, such as an adjustment in diet that requires more expensive vitamins, health data analyzer application 60 may adjust allowances in categories to compensate for additional spending on food.

Furthermore, an alternate decision making system may determine categories and allowances and transmit the categories and allowances to computer system 10 for updating financial allowances 68. For example, a banker or money manager may designate allowances for a client and transmit the allowances to computer system 10.

Conditional financial requirements may also be designated at an alternate decision making system and transmitted to computer system 10. In order for consent to make a financial purchase to be granted by health data analyzer application, any conditional financial requirements must be met. For example, a bank may place a conditional financial requirement at computer system 10 that designates that a mortgage payment be made prior to purchases in the entertainment category for a user who has not been faithful in making payments on time. In another example, a parent may place a conditional financial requirement on a child's paycheck to place a particular portion in savings prior to using the remainder for personal purchases. Alternatively, a parent may place a conditional financial requirement on a child's financial allowances where particular types of purchases must be authorized by a parent either at computer system 10 or from a remote electronic device connected to computer system 10 via a network.

Financial allowances 66 also include account information for multiple account registers controlled by a user. In making purchases, a user may designate which account information should be transmitted to complete the purchase transaction. In response to purchases made, health data analyzer application 60 adjusts the appropriate allowance category and adjusts the account register of the appropriate account to indicate a purchase. In particular, a user may make micro payments of a nominal amount via computer system 10 for usage of devices such as environment measurement monitoring system 46 or electronic exercise monitoring device 48.

Health Goals

Health allowances 68 include minimum and maximum constraints for multiple diverse categories of allowances that effect the health of a user. In particular, food allowances, medication allowances, environmental exposure allowances and exercise allowances are preferably included. Food allowances may include subcategories such as, but not limited to, serving sizes, calorie allowances, fat allowances, carbohydrate allowances, sodium allowances cholesterol allowances, protein allowances, and vitamin allowances. In addition, food allowances may indicate types of ingredients to avoid, types of ingredients to substitute, sizes of servings, number of meals per day, etc. Medication allowances may include subcategories such as, but not limited to, daily medication allowances, types of medications allowances, amounts of medications allowances. Environmental exposure allowances may include subcategories such as, but not limited to, temperature allowances, humidity allowances, wind exposure allowances, pollen exposure allowances, carbon dioxide allowances, and others. Exercise allowances may include subcategories such as, but not limited to, time allowances, heart rate allowances, blood pressure allowances, perspiration allowances, distance allowances, incline allowances, weight allowances, liquid allowances, and other allowances for bodily health measurements.

Table 3 depicts an example of health allowances 68 designated at computer system 10. As depicted, the minimum and maximum constraints are designated in correlation with one another. If a minimum is not reached or maximum is exceeded, the other categories may compensate.

As illustrated, there are five to six daily food servings to consume between 2000 and 2500 calories with a minimum of two hours between each serving. In the present example, the user has consumed 2700 calories, however burned 500 calories during the day in order to adjust for the increase in consumption. In addition, in the present example, the user has been exposed to temperatures in excess of 80° F. for one hour during the day while exercising and exercised to burn an additional 500 calories. Therefore, a user's water allowance requirement may be increased above the maximum of 90 oz. of water in order to compensate for the high temperature exposure and increased exercise. Recommendations to the user to drink additional water would be output from computer system 10.

TABLE 3

Designated Health Allowances

| Category | Subcategory | Health Allowance (Min/Max) | Current Health Usage |
|---|---|---|---|
| Food | Calories | 2000/2500 (day), | 2700 |
| Food | Servings | 5/6 (day) 2 hours between each | 6 |
| Exercise | Calories | 200/300 (day) | 500 |
| Env. Exposure | Temperature | 70° F./80° F. | 75° F./90° F. (1 hour) |
| Liquid | Water | 64 oz./90 oz. (day) | 64 oz. |

Health allowances 68 may be designated by a user according to health goals and conditions of the user. In addition, a user may select a predetermined health and/or exercise program from health reference database 64 or from an alternate source. Moreover, health data analyzer application 60 may determine minimum and maximum health allowances for a user according to health history database 62, health reference database 64, electronic schedule 66, financial allowances 68, and health profile 70. In particular, in determining minimum and maximum health allowances for health allowances 68, health data analyzer application 60 preferably attempts to balance the comprehensive health of the user.

Moreover, health allowances 68 for a user may be designated at an alternate decision making system and transmitted to computer system 10 for updating and adjusting health allowances 68. For example, a diet promotion business, such as Jenny Craig™ or Slim Fast™, may transmit recommended health allowances for a user to computer system 10 for adjusting health allowances 68. A user may designate to transmit health history database 62 to an alternate decision making system for one of these diet promotion businesses who monitor the progress of a user and may make adjustments to health allowances in order to aid the user in meeting health goals. In particular, the alternate decision making system may include an automated application to analyze progress of a user and make adjustment recommendations. In another example, a physician or exercise trainer may designate health allowances at an alternate decision making system and transmit the recommended allowances to computer system 10. In particular, a doctor may designate medication allowances that include maximum amounts of a particular medication to be consumed, times for consumption, indicators for consumption, etc.

Furthermore, a user may electronically access the menu for a future event, such as a wedding, a business meeting, a ball game, or other arena in which a particular menu of food items are planned in advance to be served. In response to receiving the menu for a future event, health data analyzer application 60 may adjust health allowances 68 in order to compensate for future menu choices.

As depicted in Table 3, minimum and maximum health allowance constraints may be controlled in relation to time. In another example, food health allowances may designate a maximum of 25 grams of fat per day, but that maximum may be further controlled across the day. The constraints may designate a maximum of 7 grams of fat between 2 AM and 10 AM, 10 grams of fat between 10 AM and 4 PM, and 8 grams of fat between 4 PM and 2 AM.

In addition to designated minimum and maximum health allowance constraints, health allowances 68 may also include conditional health requirements set by a user or authority to a user. For example, a conditional health requirement may require that a user spend at least forty-five minutes in exercise a day before enjoying a dessert with designated fat and calorie limits. In another example, a conditional health requirement may designate that if a user has been exposed to a high temperature for over thirty minutes that the user consume a particular amount of water before consuming other types of drinks or food.

Figure 4:
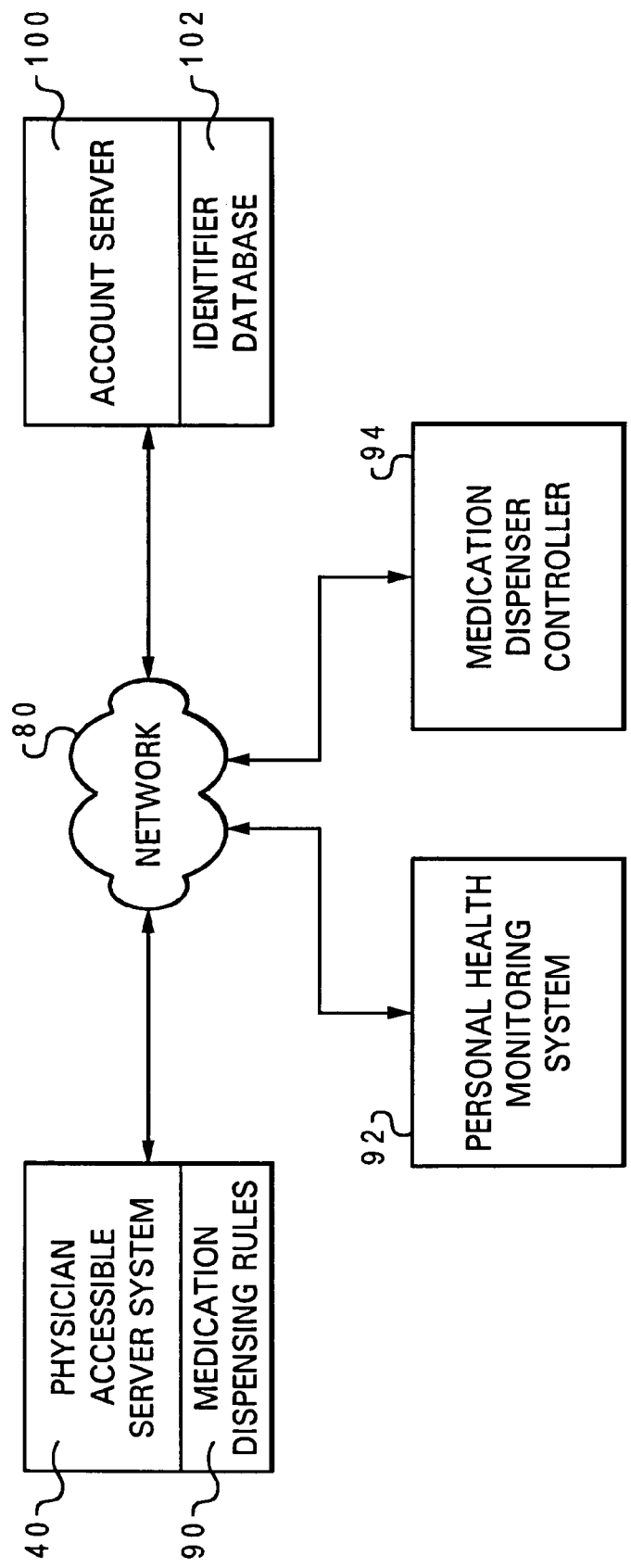
FIG. 4 illustrates a block diagram of one embodiment of a conditional health requirement system for dispensing medications in accordance with the method, system and program of the present invention.

With reference now to FIG. 4, there is depicted a block diagram of one embodiment of a conditional health requirement system for dispensing medications in accordance with the method, system and program of the present invention. As illustrated, physician accessible server system 40 includes medication dispensing rules 90 that include criteria for determining whether or not a medication should be dispensed for a particular user. In particular, criteria may be designated particularly for a user or may be universally applicable to all users.

For example, Table 4 depicts criteria including health, exercise, and/or geographical location requirements for permitting dispensing of several medications. Med1 includes a health requirement of consumption of less than 2500 calories that day and exercise for at least twenty minutes with a heart rate of greater than 120 beats per minute(bpm). Med2 includes a geographical requirement that the user is located in "region 5" which may be identified as a particular region where taking Med2 prevents illness from regional illnesses. Med3 includes a requirement of consumption of at least 60 oz. of water and location outside of a user's home region.

TABLE 4

Dispensing Criteria

| Medication | Food Requirement | Exercise Requirement | Geographical Requirement |
|---|---|---|---|
| Med1 | <2500 calories/day | >20 minutes with heart rate of >120 bpm | none |
| Med2 | none | none | located in region 5 |
| Med3 | >60 oz. water consumed | none | located outside of home region |

Physician accessible server system 40 preferably accesses health history database 62 from computer system 10 via a network 80, wherein health history database 62 is compared with medication dispensing rules 90 to determine whether or not a particular medication should be dispensed to the user. If it is determined that a medication should be dispensed to the user, then an encrypted authorization signal is transmitted from physician accessible server system 40 to medication dispenser controller 94 via network 80. Alternatively, the encrypted authorization signal may be transmitted from physician accessible server system 40 to personal health monitoring system 92 that then locally transmits the encrypted authorization signal to medication dispenser controller 94.

Medication dispenser controller 94 preferably includes a control mechanism for disabling access to medication enclosed in a medication dispenser unless an authorization signal is received that is understood by medication dispenser controller 94 to allow access to the medication. In particular, the medication dispenser may be provided to the user with a prescription medication or may be available at a pharmacy location.

An account server 100 accessible via network 80 includes an identifier database 102. For each server or device connected directly to network 80 there is preferably a network address associated with the server or device that is included in identifier database 102. In particular, each network address may be associated with one or more alphanumeric identifiers that may be looked up in identifier database 102 in order to determine the associated network address. For example, personal health monitoring system 92 may be located at network address "01.988.876.92" and associated with a universal alphanumeric identifier such as "lumberg-ritty.alpha.ind". Therefore, in order for physician accessible server system 40 to transmit a medication authorization signal to personal health monitoring system 92, the universal alphanumeric identifier associated with personal health monitoring system 92 is transmitted to account server 100 in order to determine the network address associated with the universal alphanumeric identifier. The medication authorization signal may then be transmitted to the associated network address.

In particular, a universal alphanumeric identifier for a particular user may be accessible via computer system 10 or may be affixed to the user in some form, such as an identification bracelet. Preferably, the universal alphanumeric identifier provides access to a secured portion of a user's health profile.

For example, a person with a heart condition may have a universal alphanumeric identifier engraved in a tag worn by the user that can be utilized by a medical professional to access a user's health profile. Advantageously, if the person is suffering from health problems, a medical professional can utilize the universal alphanumeric identifier via network 80 to access the person's health profile in order to better treat the person.

Health Profile

Returning now to FIG. 2, health profile 70 includes a current status of the comprehensive health of a user. As previously described, health data analyzer application 60 determines health effecting factors and averages for a user from health history database 62 and includes the health effecting factors and averages in health profile 70. In addition, health profile 70 includes a record of tasks performed and not performed, actions selected, health and environmental parameters received and control signals transmitted to health effecting devices. Moreover, health profile 70 also includes persona data about a user including age, sex, height, allergies, injuries, health care provider information, employment information and other personal data. Furthermore, health profile 70 includes summaries of electronic schedule 66, financial allowances 67, and health allowances 68. Health data analyzer application 60 advantageously utilizes the personal data in health profile 70 in analysis.

In particular, there are individuals from whom a health profile might be of interest to others. Therefore, a filtered version of health profile 70 may be output where any individual might access health profile 70 for a fee or advertisers of products included in health profile 70 may market health profile 70. For example, athletes may be interested in viewing a health profile for Michael Jordan in order to establish time, financial and health allowances that have been used by Michael Jordan. Products utilized by Michael Jordan may be designated in health profile 70 such that individuals viewing the health profile may follow Michael Jordan's example.

User Preferences

A user's preferences in multiple diverse categories are included in electronic preferences 72. Examples of preference categories may include, but are not limited to including, medication preferences, cooking preferences, food preferences, restaurant preferences, retailer preferences, brand preferences, travel preferences, environmental preferences, exercise preferences, entertainment preferences, and other categories of preferences as designated by a user. Health data analyzer application 60 may utilize electronic preferences 72 in analyzing selectable actions for a user and in determining control signals to transmit to health effecting devices. For example, health data analyzer application 60 may determine a user's preferred air conditioning temperature setting from electronic preferences 72 and transmit the temperature preference to an environmental control system 56 that controls the air conditioning temperature. In another example, health data analyzer application 60 may determine a user's preferred food items and filter an electronic menu received from a restaurant menu server 42 according to the user's food preferences in addition to filtering according to financial allowances 67 and health allowances 68.

Controlling Health Related Devices

Device controllers 74 may be included in computer system 10 that preferably format and direct transmission of control signals and requests for data from computer system 10 to multiple diverse devices. In the present embodiment, control signals and requests for data are advantageously transmitted in the XML data format, however other data formats may be utilized. In addition, in the present embodiment, a pharmacy accessible server 50, a food order server 52, a health control device 54, an environment control system 56, an authority-enabled system, an exercise machine controller 58, and an electronic market system 59 are examples of devices to which device controllers 74 may direct transmissions of control signals and requests for data.

Figure 5:
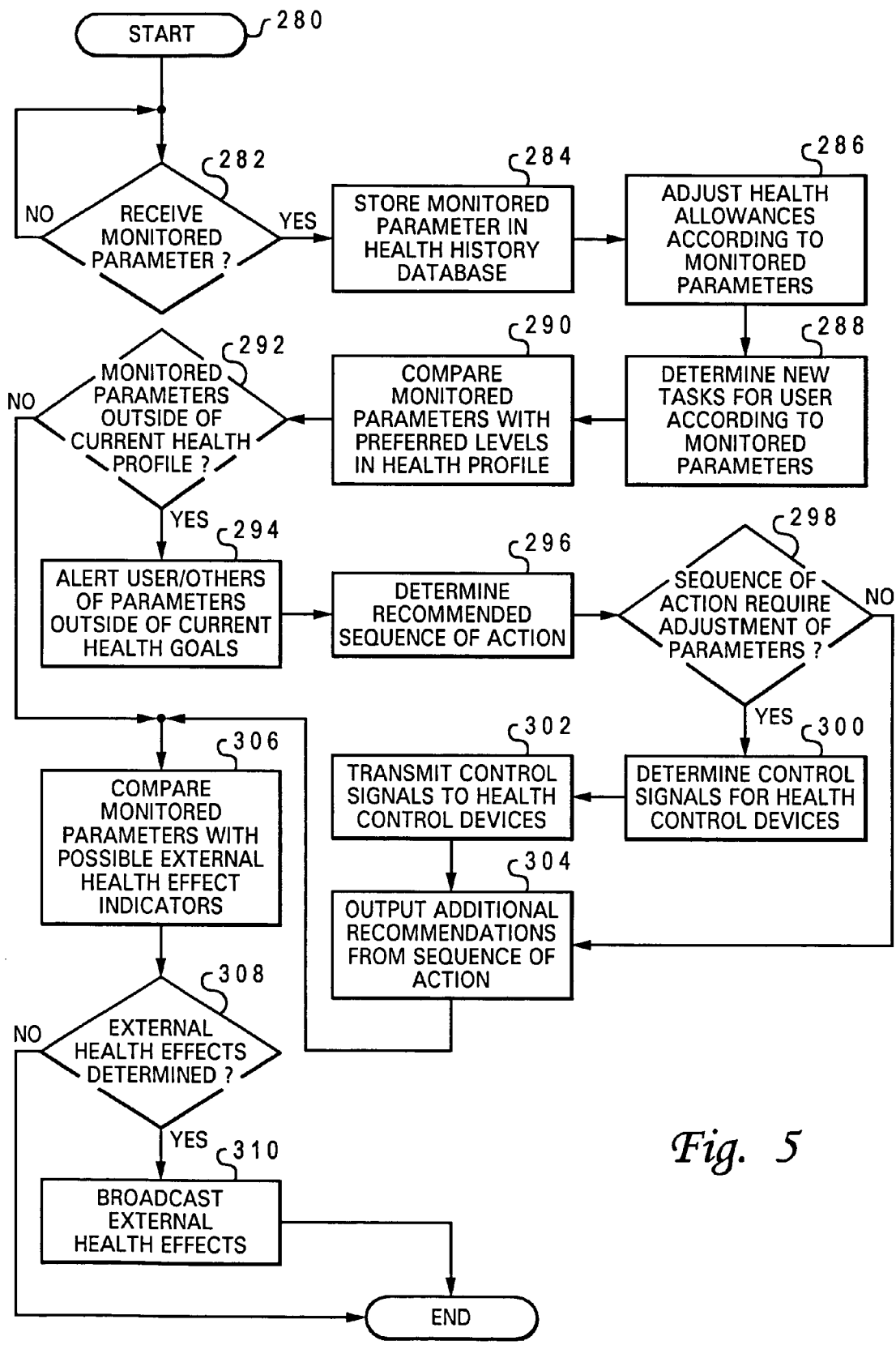
FIG. 5 depicts a high level logic flowchart of a process and program for responding to monitored physical and environmental parameters in accordance with the present invention.

With reference now to FIG. 5, there is depicted a high level logic flowchart of a process and program for responding to monitored physical and environmental parameters in accordance with the present invention. As illustrated, the process starts at block 280 and thereafter proceeds to block 282. Block 282 depicts a determination as to whether or not a monitored parameter is received. If a monitored parameter is not received, then the process iterates at block 282. If a monitored parameter is received, then the process passes to block 284.

Block 284 illustrates storing the monitored parameter in the health history database. Next, block 286 depicts adjusting the health allowances according to the monitored parameter. Thereafter, block 288 illustrates determining new tasks for the user according to the monitored parameters. Next, block 290 depicts comparing the monitored parameter with preferred parameter levels designated in the user's health profile; and the process passes to block 292.

Block 292 depicts a determination as to whether or not the monitored parameter is outside of the preferred parameter levels. If the monitored parameter is not outside the preferred parameter levels, then the process passes to block 306. If the monitored parameter is outside the preferred parameter levels, then the process passes to block 294.

Block 294 illustrates alerting the user and others that the monitored parameter is outside of the preferred parameter levels. Next, block 296 depicts determining a recommended sequence of actions in view of the heath reference database recommendations and actions designated in the user's health profile. Thereafter, block 298 illustrates a determination as to whether or not the recommended sequence of action includes adjustment of a physical and/or environmental parameter by a health related device. If the sequence of action does not include adjustment of a physical and/or environmental parameter, then the process passes to block 304. If the sequence of action does include adjustment of a physical and/or environmental parameter, then the process passes to block 300.

Block 300 depicts determining a control signal for at least one health related device in order to adjust physical and/or environmental parameters. Next, block 302 illustrates transmitting the control signal to the appropriate health related devices. Thereafter, block 304 depicts outputting additional recommendations from the recommended sequence of action; and the process passes to block 306.

Block 306 illustrates comparing the monitored parameter with possible external health effect indicators. External health effect indicators may represent indicators of physical or mental illness that may effect others within a particular proximity of the user. Next, block 308 depicts a determination as to whether or not any external health effects are determined. If no external health effects are determined, then the process ends. If external health effects are determined, then the process passes to block 310. Block 310 illustrates broadcasting the external health effects; and the process ends.

Global Positioning

Global positioning system 76 may be included with computer system 10 in order to passively detect the global position of computer system 10. Detected global positions are preferably stored in health history database 62 and analyzed by health data analyzer application 60. In particular, health data analyzer application 60 may determine exercise performed by a user, such as running, and the rate of travel. In addition, computer system 10 may receive a transmission from a news network detailing environmental hazards, exposure areas, and dates which health data analyzer application 60 utilizes to compare with a user's tracked global positions in order to determine whether or not a user has been exposed to any health effecting hazards. In another example, the news network may detail fast moving storms such that a user may be alerted to move indoors and outdoor events may be rescheduled. In particular, if each member of a sports team carries a personal health monitoring system and a storm is headed towards the practice field for the team, then each personal health monitoring system would receive an alert for the storm, would determine when practice can be rescheduled and transmit the recommended times among personal health monitoring systems such that practice can be rescheduled according to schedules for each team member.

In yet another example, the use of global positioning data may be utilized in conjunction with physical and environmental parameters to determine areas where a user reacts to allergies in order to determine the cause of allergies and what level of the allergen affects the user.

In yet another example, global positioning data, and in particular altitude, may be utilized to adjust an exercise schedule, health allowances for fluids and foods, and other allowances that would be affected by a significant increase or decrease in altitude. For example, if a user has scheduled a trip to a high altitude location in electronic schedule 66, the health data analyzer application 60 may adjust allowances that will prepare the user's body for the increase to a high altitude location.

Moreover, conditional requirement may include factors dependent upon a user's global position. For example, a parent may include a conditional financial requirement that limits a child from utilizing financial allowances 67 unless the child was detected at school during school hours. In particular, computer system 10 may be equipped with a biometric or other device that is enabled to detect whether or not computer system 10 is within a proximity of a user.

Broadcasting in a Local Area

Transceiver 78 may be included with computer system 10 in order to transmit and receive signals within a local area. In one example, transceiver 78 may be utilized to broadcast factors of a user's current health that may effect others, such as chicken pox or a high temperature, as described in FIG. 5. In another example, transceiver 78 may be utilized to broadcast electronic preferences 72 such that retailers and others within a particular proximity of computer system 10 may detect the preferences and specialize services and products provided to the user.

In addition, transceiver 78 may be utilized to receive local broadcasts, such as from a local health clinic. In particular, it is advantageous for transceiver 78 to detect broadcasts from local health clinics that include a location, current environmental factors, health related recommendations for the area, recommended immunizations, and health services available. Health data analyzer application 60 may compare current environmental factors and health related applications with health history database 62, health allowances 68 and health profile 70 in order to determine whether or not a user is at risk from exposure to a particular environment or needs to respond to health related recommendations.

For example, a user traveling through Colorado may receive broadcasts from local health clinics that indicate current environmental conditions and health related recommendations such as warnings for those with heart conditions and recommendations to increase fluid intake. In addition, these local health clinics may indicate the proximity of specialists, such as heart specialists. Health data analyzer application 60 would advantageously increase minimums for fluid allowances in health allowances 68 and if the user's health profile 70 indicates heart conditions, determine the risk of continuing to increase in altitude. In addition, a physician for the user may include a conditional health requirement that requires a user to be within a particular proximity of a heart specialist in order to continue an increase in altitude. Health data analyzer application 60 would compare the current global position of the user with the proximity of a heart specialist broadcasted by the local health clinic to determine if the conditional requirement would allow an increase in altitude.

Prioritizing Selectable Actions

As previously described, health data analyzer application 60 is enabled to analyze multiple diverse types of selectable actions for a user in view of balancing a user's comprehensive health. In addition, particular types of selectable actions may be designated to be prioritized by an alternate decision making system.

Figure 6:
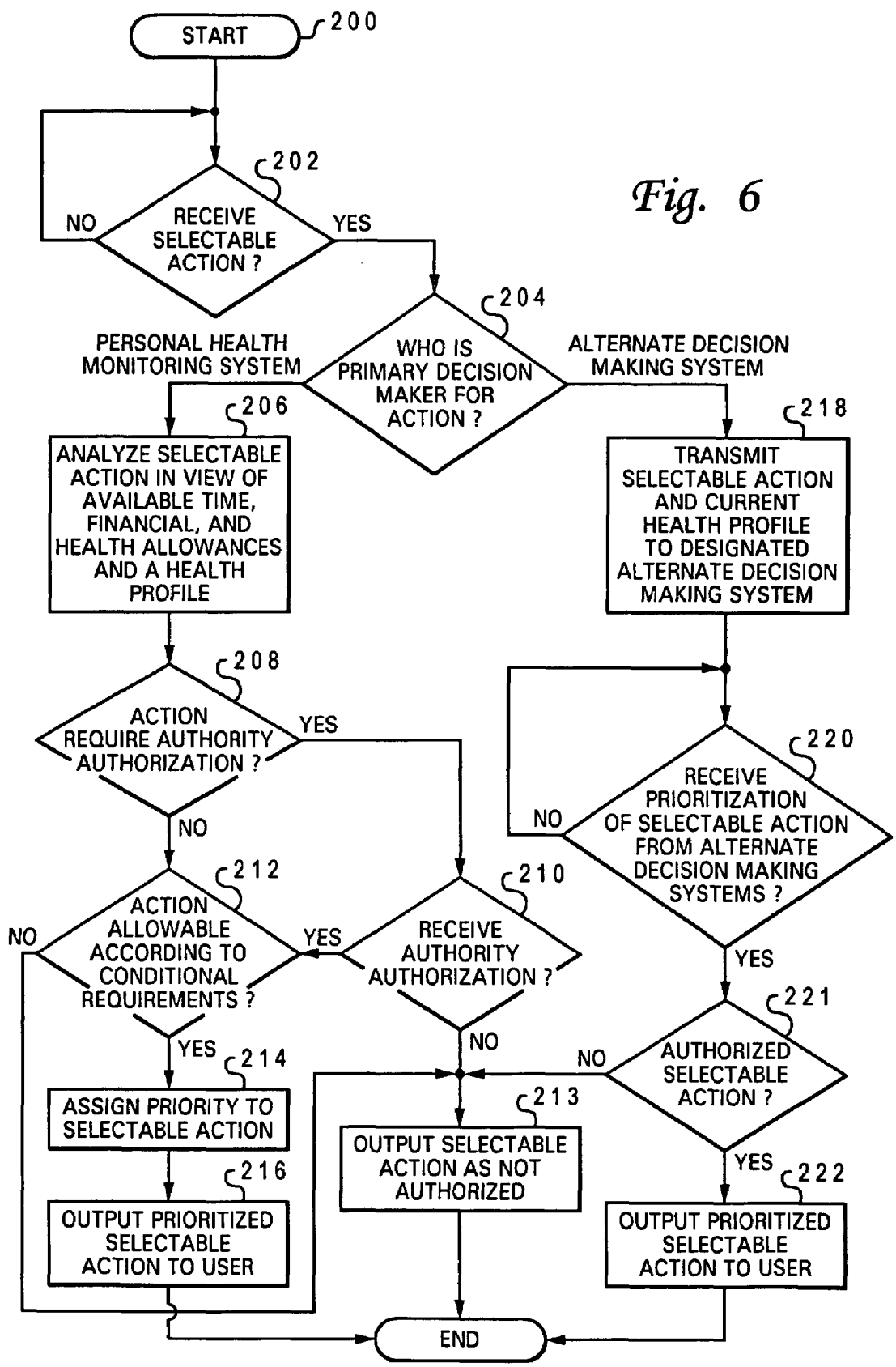
FIG. 6 illustrates a high level logic flowchart of a process and program for prioritizing selectable actions in accordance with the present invention.

Referring now to FIG. 6, there is depicted a high level logic flowchart of a process and program for prioritizing selectable actions in accordance with the present invention. As depicted, the process starts at block 200 and thereafter proceeds to block 202. Block 202 illustrates a determination as to whether or not a selectable action is received. Multiple selectable actions may be received together. If a selectable action has not been received, then the process iterates at block 202. If at least one selectable action has been received, then the process passes to block 204.

Block 204 depicts a determination as to who is the designated decision maker for the selectable action. If the selectable action is designated for decision making by the personal health monitoring system, then the process passes to block 206. If the selectable action requires decision making by an alternate decision making system, then the process passes to block 218.

Block 206 illustrates analyzing the selectable action in view of the available time, finances, and health allowances and health profile for the user in order to determine prioritization of the selectable action. Next, block 208 depicts a determination as to whether or not the selectable action requires authority authorization. If the selectable action requires authority authorization, then the process passes to block 210. If the selectable action does not require authority authorization, then the process passes to block 212.

Block 210 depicts a determination as to whether or not authority authorization is received. In particular, an authority may enter an authorization at the user's personal health monitoring system or may transmit authorization from a remote device via a network. If authority authorization is not received, then the process passes to block 213. Block 213 illustrates outputting that the selectable action is not allowed; and the process ends. If authority authorization is received, then the process passes to block 212.

Block 212 illustrates a determination as to whether or not the selectable action is allowable according to any conditional time, financial and/or health requirements. If the selectable action is not allowable according to any conditional requirements, then the process passes to block 213. If the selectable action is allowable according to any conditional requirements, then the process passes to block 214.

Block 214 depicts assigning a priority to the selectable action. Next, block 216 illustrates outputting the prioritized selectable action to the user; and the process ends. In outputting prioritized actions to the user, multiple forms of prioritization may be utilized. For example, selectable actions may be depicted in order from a highest priority number to a lowest priority number. In addition, a graphical differentiation may be made between higher and lower priority selectable actions, such as green highlighting for high priority selectable actions and blue highlighting for lower priority selectable actions.

Block 218 depicts transmitting the selectable action and current health profile to a designated alternate decision making system. Next, block 220 illustrates a determination as to whether or not prioritization of the selectable action is received from an alternate decision making system. If prioritization is not received, then the process iterates at block 220. If prioritization is received, then the process passes to block 221. Block 221 depicts a determination as to whether or not the prioritized selectable actions are authorized if authorization is required. If the selectable actions are not authorized and authorization is required, then the process passes to block 213. If the selectable actions are authorized and authorization is required, then the process passes to block 222. Block 222 depicts outputting the prioritized selectable action to the user; and the process ends.

Alternate Decision Making Systems

Figure 7:
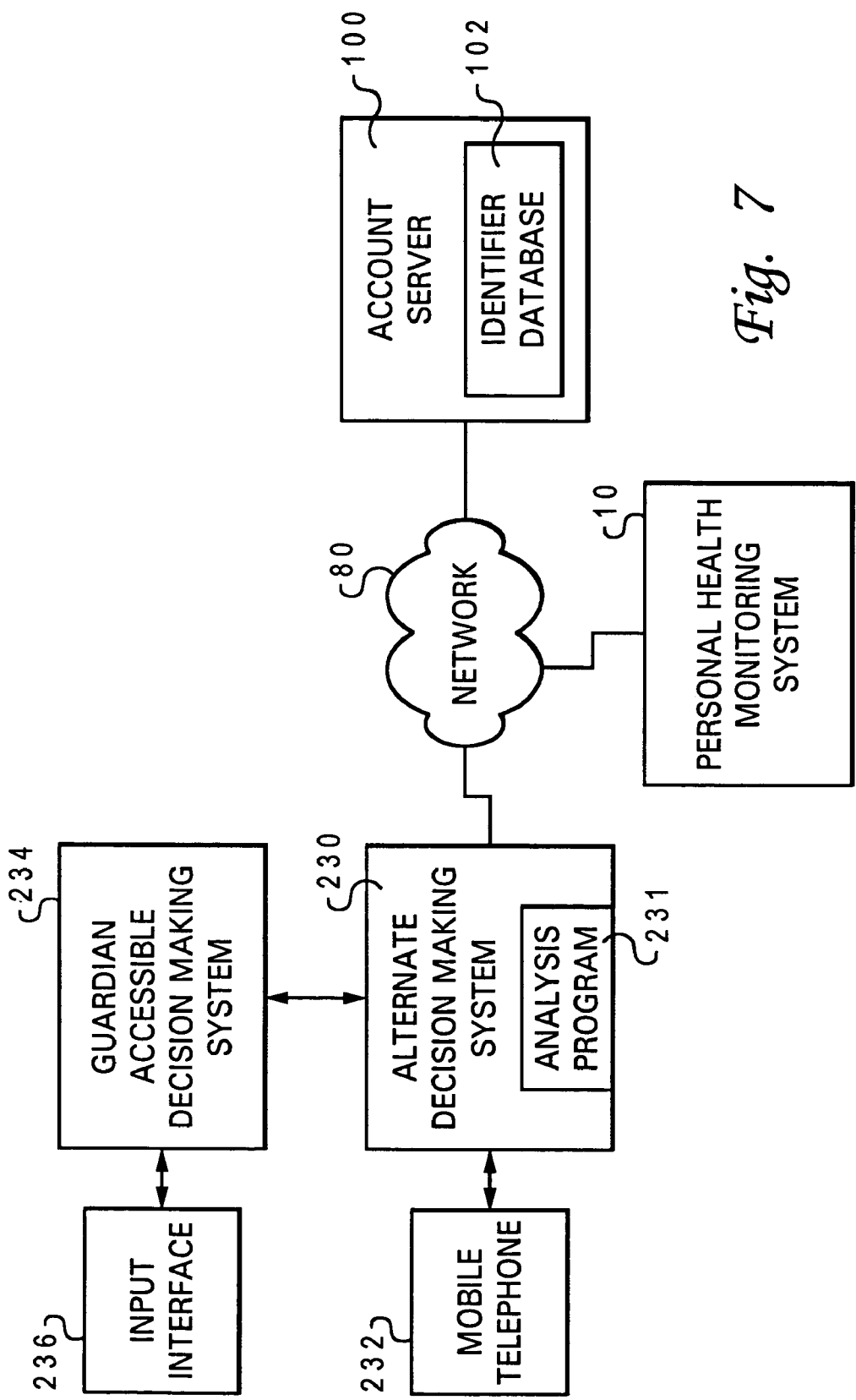
FIG. 7 depicts a block diagram of one embodiment of a cluster of alternate decision making systems in accordance with the method, system and program of the present invention.

With reference now to FIG. 7, there is depicted a block diagram of one embodiment of a cluster of alternate decision making systems in accordance with the method, system and program of the present invention. As illustrated, computer system 10 communicates with an alternate decision making system 230 via network 80. In the particular example, alternate decision making system 230 includes an analysis program 231 that analyzes a user's current health profile and the selectable actions to be prioritized and determines whether or not an authority to the user needs to be notified or if the authority needs to provide authorization for one or more of the selectable actions.

If an authority needs to be notified or provide authorization, a transmission to the authority's mobile telephone 232 is controlled by alternate decision making system 230. The authority is then enabled to authorize one or more selectable actions from mobile telephone 232. While in the present embodiment the authorization request is transmitted to mobile telephone 232, in alternate embodiments, the authorization request may be transmitted to other electronic devices including, but not limited to personal digital assistants (PDAs), digital pagers, portable computers, electronic watches, etc.

In addition, analysis program 231 may determine that a guardian to the user needs to further provide authorization for one or more the selectable actions. Therefore, alternate decision making system 230 would control transmission of the one or more selectable actions and the user's current health profile to a guardian accessible decision making system 234. A guardian is enabled to authorize and/or prioritize the one or more selectable actions at guardian accessible decision making system 234 via an input interface 236, for example.

Decisions made at alternate decision making system 230 and guardian accessible decision making system are transmitted to computer system 10 via network 80 and utilized by computer system 10 to direct a user in making selections from selectable actions. In particular, the present embodiment is particularly applicable for a medication order authorization where the physician authorizes a medication via telephone 232 and a parent then authorizes a child to purchase the authorized medication via input interface 236.

Figure 8:
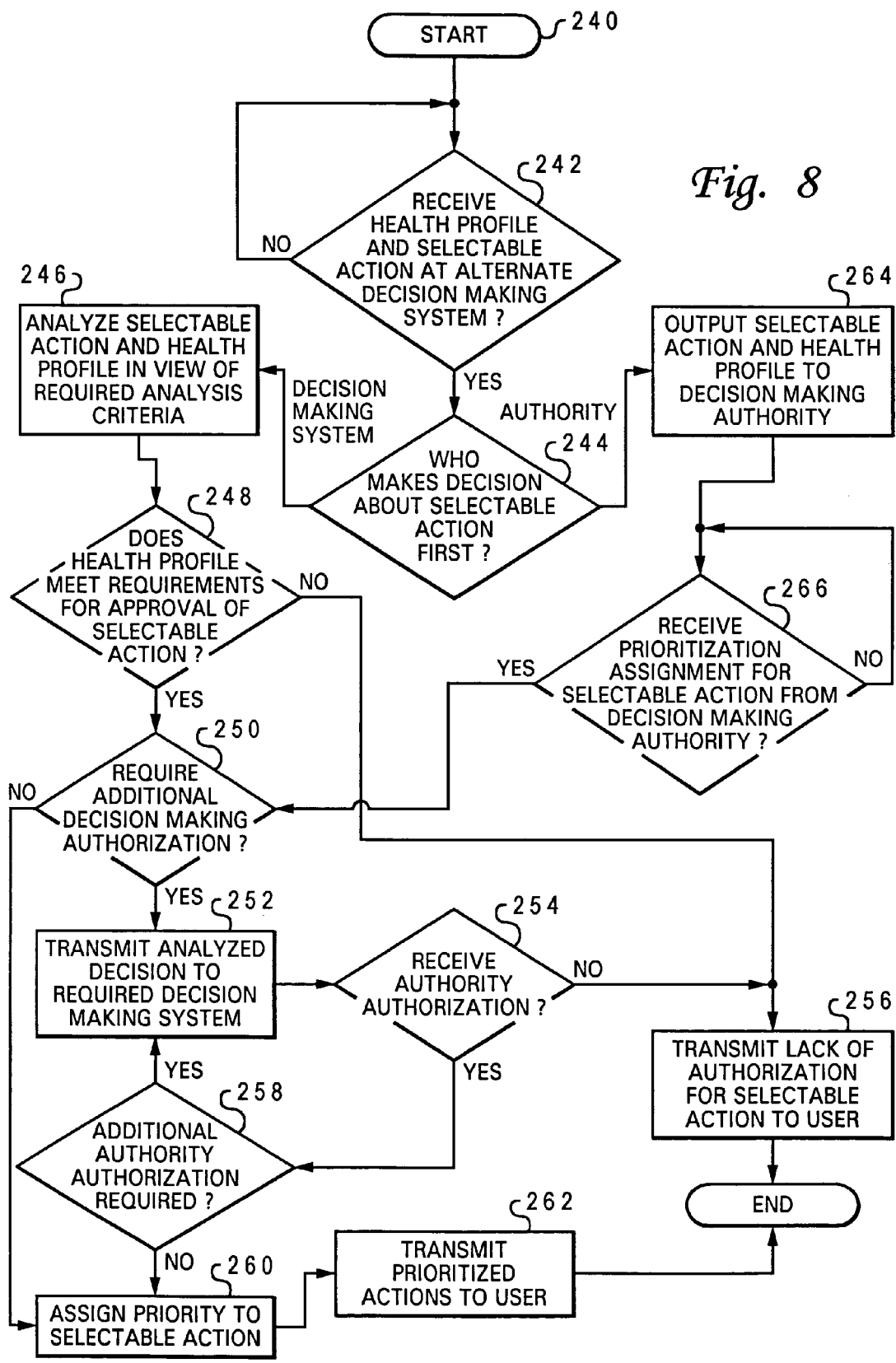
FIG. 8 illustrates a high level logic flowchart of a process and program for making decisions about selectable actions at alternate decision making systems in accordance with the present embodiment.

Referring now to FIG. 8, there is illustrated a high level logic flowchart of a process and program for making decisions about selectable actions at alternate decision making systems in accordance with the present embodiment. As depicted, the process starts at block 240 and thereafter proceeds to block 242. Block 242 illustrates a determination as to whether or not a health profile and at least one selectable action are received at an alternate decision making system. If a health profile and at least one selectable action are not received, then the process iterates at block 242. If a health profile and at least one selectable action are received, then the process passes to block 244.

Block 244 depicts a determination as to who makes a decision about the selectable action first. If the alternate decision making system is designated to analyze the selectable action first, then the process passes to block 246. If a user is designated to make decisions about the selectable action first, then the process passes to block 264.

Block 264 illustrates outputting the selectable action and health profile to the decision making authority via an output interface, electronic device, etc. Next, block 266 depicts a determination as to whether or not a prioritization assignment for the selectable action is received from the decision making authority. If a prioritization assignment for the selectable action has not been received, then the process iterates at block 266. If a prioritization assignment for the selectable action has been received, then the process passes to block 250.

Block 246 illustrates analyzing the selectable actions and health profile in view of designated analysis criteria at the alternate decision making system in order to determine prioritization of the selectable action. Next, block 248 depicts a determination as to whether or not the health profile meets requirements for approval of the selectable action. For example, if the health profile indicates that a user is exceeding daily health allowances for calories and fat and the designated analysis criteria requires that a user does not exceed the designated health allowances for calories and fat in order to receive authorization for the selectable action, then it would be determined that the health profile does not meet requirements for approval of the selectable action.

Therefore, if the health profile does not meet requirements for approval of the selectable action, then the process passes to block 256. Block 256 illustrates transmitting a lack of authorization for the selectable action to the user. If the health profile does meet requirements for approval of the selectable action, then the process passes to block 250.

Block 250 depicts a determination as to whether or not the selectable action requires an additional authorization from another alternate decision making system. If the selectable action does not require additional authorization, then the process passes to block 260. If the selectable action does require additional authorization, then the process passes to block 252. Block 252 depicts transmitting the analyzed decision to the next designated alternate decision making system. Next, block 254 illustrates a determination as to whether or not authority authorization is received. If authority authorization is not received, then the process passes to block 256. If authority authorization is received, then the process passes to block 258.

Block 258 depicts a determination as to whether or not an additional authorization is required. If an additional authorization is required, then the process passes to block 252. If no additional authorization is required, then the process passes to block 260. Block 260 illustrates assigning an overall priority to the selectable action according to all alternate decision making systems. Next, block 262 depicts transmitting the prioritized decision to the user; and the process ends.

Health Related Inputs

Returning now to FIG. 2, Computer system 10 may receive inputs in the form of selectable actions, tasks, and health and environmental parameters from multiple diverse input devices. In the present embodiment computer system 10 may receive selectable action inputs from devices including, but not limited to, physician accessible server 40, restaurant menu server 42, electronic exercise monitoring device 48, electronic recipe server 49 and alternate decision making systems. Computer system 10 may receive tasks from devices including, but not limited to, physician accessible server 40, alternate decision making systems, and via user input to an input interface 36. In addition, computer system 10 may receive health and environmental parameters from devices including, but not limited to, health measurement monitoring device 44 and electronic environment measurement device 46.

Medications

As described in U.S. patent application Ser. No. 09/560,992, herein incorporated by reference, physician accessible server 40 provides a server system from which a physician or other health professional may transmit an encrypted medication order for a prescription medication, over-the-counter medication, or vitamin to computer system 10 in association with a particular user in the form of selectable action for the user. The medication order is preferably transmitted from physician accessible server 40 to computer system 10 in a transmittable data format, such as XML.

The user is preferably enabled to select a pharmacy or other medication provider to which the encrypted medication order is to be transmitted from computer system 10. For example, an encrypted medication order may be selected for transmission from computer system 10 to pharmacy accessible server 50, where pharmacy accessible server 50 is accessible to a medication provider enabled to decrypt the medication order. In addition, electronic preferences 72 may include a preferred medication provider designated by the user to which medication orders are automatically transmitted unless a user is detected outside of a normal geographical range.

A task for taking the medication is also included with the medication order and is preferably added to electronic schedule 66 in correlation with food and exercise requirements that may be associated with the medication. For example, if a medication needs to be taken thirty minutes before each meal for ten days, then health data analyzer application 60 would add a task to electronic schedule 66 at thirty minutes before each meal time to remind the user to take the medication. If a meal time is rescheduled during the ten days, the task for taking the medication would automatically be rescheduled accordingly. In addition, the task for taking the medication may include a conditional scheduling and/or health requirement that is added with the task to electronic schedule 66.

In addition, computer system 10 may transmit comprehensive health data including health history database 62, electronic schedule 66, financial allowances 67, health allowances 68, health profile 70, and/or electronic preferences 72 to physician accessible server 40. Preferably, a physician or other medical professional is enabled to access health related data received from computer system 10 at physician accessible server 40. A physician or other medical professional may utilize the health related data received at physician accessible server 40 in analyzing a user's health. In addition, physician accessible server 40 may include additional analysis applications that aid a physician in automated analysis of a user's health.

In particular, the comprehensive health data for a user received at physician accessible server 40 may be accessible to a psychologist, counselor, or other mental health professional in order to determine factors that may be influencing a person's mental health and transmit recommendations for changing a user's schedule, finances, or health allowances in order to adjust a user's mental health. In addition, physician accessible server 40 may determine medications that are suitable for treating mental health problems according to the user's health profile 70.

The present invention is particularly advantageous to a physician when comprehensive health data for multiple family members is accessible at physician accessible server 40. Additional analysis applications at physician accessible server 40 may aid a physician in determining health effecting factors that are common among a family. In addition, recommended health goals and medication may be determined in order to prevent a younger member of a family from suffering from preventable illness that is present in older members of the family.

Additional analysis applications at physician accessible server 40 preferably aid a physician in determining preferred medications for a user in order to balance a user's comprehensive health. For example, if more than one brand or type of a particular medication is available, then physician accessible server 40 would determine which of the multiple available medications will best fit in a user's schedule, best fit in a user's price range, and not include side effects that are adverse according to the user's health profile 70. For example, a generic medication may be selected over a brand name medication by physician accessible server 40 if a user's financial allowances for medication does not provide for the expense of the brand name medication. However, if the generic medication includes side effects adverse to the user that are not included in the brand name medication, physician accessible server 40 may recommend the brand name medication or provide a comparison of the constraints associated with the generic versus the brand name medication.

In addition, in determining preferred medications, electronic preferences 72 preferably indicates a user's preference for the state of the medication, for example a preference for a pill or liquid form, that is utilized by physician accessible server 40. In addition, electronic preferences 72 may indicate a user's preference to always receive a medication order for a generic medication if available.

Electronic preferences 72 and health profile 70 may be particularly advantageous for a physician in determining a user's preferences for treatment. For example, electronic preferences may indicate that a user prefers not to be resuscitated or a particular person or person's from whom blood is preferred if needed. Health profile 70 may indicate a user's type of blood, whether not the user is an organ donor, a user's typical pain threshold, etc. Physician accessible server 40 preferably filters through electronic preferences 72 and health profile 70 and alerts a physician of particularly relevant preferences and history for treatment of the patient.

Prepared Foods

As described in U.S. patent application Ser. No. 09/466,000, herein incorporated by reference, restaurant menu server 42 provides a server system from which computer system 10 receives multiple selectable actions from an electronic food menu for a restaurant of a group of restaurants in a transmittable data format, such as XML. Advantageously, each food menu item in the electronic food menu includes a breakdown of all ingredients, nutritional characteristics, price, time to table, and other data that is relevant to the food menu item. In the present invention, health data analyzer application 60 preferably analyzes each food menu item in view of electronic schedule 66, financial allowances 67, health allowances 68, health profile 70, and electronic preferences 72 to determine recommended food menu items from the electronic food menu.

A travel time to a restaurant, delivery time, and/or estimated wait time may be compared with electronic schedule 66 by health data analyzer application 60 to determine recommended restaurants. In addition, health data analyzer application 60 may compare a time to table with electronic schedule 66 to determine if the user has sufficient time to wait for the food menu item and eat at a preferred pace.

Health data analyzer application 60 may compare financial allowances 67 for food items with prices of each food menu item in order to determine recommended food menu items. In particular, if a user is at a restaurant where food menu items are more costly than a financial allowance for that meal, then health data analyzer application 60 would redistribute allowances, such that the user is able to select from the electronic food menu.

In addition, health data analyzer application 60 compares health allowances 68 with the breakdown of ingredients and nutritional characteristics of each food menu item to determine recommended food menu items. In particular, if there are not any food menu items that are recommended in view of food allowances for the current meal, health data analyzer application 60 may redistribute food allowances or exercise allowances in order to provide recommended food menu items to the user. In addition, health data analyzer application 60 may recommend a food menu item that is equivalent to more than one portion suitable for the user, such that the user may save a portion of the meal for another meal or meals.

Health data analyzer 60 may also determine recommended combinations of food menu items according to price and health allowances. For example, salad A at $2.50, salad B at $4.00, entree C at $3.00 and entree D at $4.50 are all recommended food menu items according to price and health allowances. If the financial allowance for the meal is $7.00, then a combination of salad A and entree D, or salad B and entree C may be recommended.

Food menu items and combinations thereof that are determined by health data analyzer application 60 may be further filtered according to a user's electronic preferences 72. For example, a user may designate preferred types of foods and restaurants. In addition, the service that a user receives may be determined by a restaurant, such as preferred types of restaurants, preferred seating in restaurants, preferred wait persons, etc. from electronic preferences 72.

A user may select a food menu item or combination of food menu items for consumption at computer system 10 via input interface 36. The user's menu selections are preferably transmitted to a food order server 52 that is associated with a restaurant providing the electronic food menu selected from. The user's order is placed in a queue of orders to be prepared at the restaurant. In one embodiment, in response to a user ordering food menu items, health history database 62, financial allowances 67 and health allowances 78 are adjusted to reflect the food menu items ordered. In another embodiment, a user may indicate after eating what portion of food menu items were consumed at computer system 10, wherein health history database 62 and health allowances 78 are adjusted to reflect the percentage of food actually consumed.

Home Cooked Foods

As described in U.S. patent application Ser. No. 09/560,374, herein incorporated by reference, electronic recipe server 49 provides a database of selectable electronic recipes including ingredient listings, nutritional content breakdowns, preparation times, and cook times. Computer system 10 accesses electronic recipe server 49 and retrieves selected recipes in a transmittable data format, such as XML. Electronic recipes accessible via electronic recipe server 49 may be searched by type, ingredients, nutritional content, preparation times, cook times and other search criteria designated by a user. In addition, electronic recipes accessible via electronic recipe server 49 may be grouped by recommended meal plans.

Health data analyzer application 60 analyzes the electronic recipes to determine recipes with nutritional content that falls within the constraints designated in health allowances 68. In addition, health data analyzer application 60 further analyzes the electronic recipes according to preparation and cook times in view of electronic schedule 66, such that electronic recipes that can be added to a user's schedule are selected. Moreover, health data analyzer application analyzes the ingredients of the electronic recipes according to financial allowances 67, such that electronic recipes whose ingredients are within the financial constraints for the user are selected.

Additional analysis criteria may also include electronic preferences 72 that includes food preferences for a user and supplies 73 that includes kitchen supplies and food supplies accessible to a user. For example, a user may prefer particular vegetables, such that vegetable recipes are further analyzed and selected according to the user's preferred vegetables. In another example, if a user needs a recipe for dinner that night, recipes that utilize kitchen appliances and cooking accessories in addition to ingredients that are accessible to the user at the user's household, may be recommended to the user.

Health data analyzer application 60 may couple recommended electronic recipes in order to provide recommended meal plans for a user. For example, recommended meal plans may include a salad recipe, a meat recipe and a bread recipe. In addition, health data analyzer application 60 may include pre-packaged foods in recommended meal plans. For example, a recommended meal plan may include a can of fruit, a potato salad recipe, a sandwich recipe and a pre-packaged light dessert.

A user may select tasks of multiple meal plans of electronic recipes and pre-packaged foods to add to electronic schedule 66 for future preparation and cooking. Preferably, an inventory monitor 47 monitors the current kitchen supply and food supply inventory accessible to a user as described in U.S. patent application Ser. No. 09/560,320, herein incorporated by reference. Therefore, health data analyzer application 60 may determine what kitchen and food supplies that are needed for the scheduled meal plans are not included in inventory.

As described in U.S. patent application Ser. No. 09/560, 319, herein incorporated by reference, requests for kitchen and food supplies that are needed for inventory may be transmitted from computer system 10 to at least one electronic market system, such as electronic market system 59. Electronic market system 59 includes a database of items for purchase and responds to requests from computer system 10 with an offering of available items that are requested by the user. In particular, requests for kitchen and food supplies may be transmitted according to preferred market systems and preferred brands of items designated in electronic preferences 72.

Advantageously, each purchase made via computer system 10 at electronic market system 59, pharmacy accessible server 50, or food order server 52 is tracked in health history database 62 according to the product distributor. For example, toothpaste purchased via an on-line market A is recorded in health history database 62 in association with market A. Therefore, any illnesses which may be born from a faulty product can be traced back to the product distributor. In addition, as will be further described, the health history databases from multiple individuals may be compared at a health tracking system in order to further determine the manufacturer or grower of the faulty product. For example, it may be determined that the manufacturer that provided the faulty toothpaste to market A was toothpaste manufacturer B.

Bodily Health

As described in U.S. patent application Ser. No. 09/560, 374, herein incorporated by reference, electronic health measurement monitoring device 44 provides a device for monitoring a physical bodily health parameter of a user. Examples of bodily health parameters include, but are not limited to, body temperature, blood pressure, blood sugar level pulse rate, respiration rate, tactile agility, and flexibility. Bodily health parameters detected at health monitoring device 44 may be transmitted to computer system 10 in a transmittable data format, such as XML. Computer system 10 advantageously stores the bodily health parameters received from health monitoring device 44 in health history database 62.

Health data analyzer application 60 analyzes the bodily health parameters in view of health allowances 68 to determine if the health parameters fall within constraints designated in health allowances 68. Health data analyzer application 60 also analyzes the bodily health parameters in view of health profile 70 to determine if any warnings are included in association with certain levels of bodily health parameters.

If the bodily health parameters do not fall within designated constraints or are at warning levels, a warning to the user and recommendations may be output from computer system 10. In addition, health data analyzer application 60 may determine control signals for transmission to a health control device 54 in order to adjust the bodily health parameter that is not acceptable. For example, if a user's blood sugar reading is below an acceptable constraint and the user's health profile 70 indicates that the user should receive an injection of glucose at that level, then health data analyzer application 60 will determine a control signal for transmission to a glucose dispenser to dispense the appropriate amount to the user.

Health data analyzer application 60 may advantageously analyze health history database 62 in view of bodily health parameters in correlation with a user's geographic location and tasks in order to determine health effecting factors and emotionally effecting factors for the user. For example, if it is determined by health data analyzer application 60 that a user's blood pressure exceeds a maximum blood pressure allowance every time that the user's child has a scheduled athletic event, then it may be determined that the attending the athletic event is a health effecting factor that is detrimental to the user. In another example, if it is determined that a user's blood sugar drops within thirty minutes after lunch when the user eats a particular meal, then it may be determined that the particular meal should not be consumed by the user at lunch even though the meal may meet health and/or financial allowances. In yet another example, differentiated levels of anxiety, sadness and other emotions may be determined to be associated with body temperature and pulse rates. In particular, a mental health professional utilizes emotion-indicating-bodily-health parameters in association with particular tasks to determine areas in which a user may benefit from counseling or use of a medication.

Environmental Exposure

As described in U.S. patent application Ser. No. 09/560, 163, herein incorporated by reference, electronic environment measurement device 46 provides a device for monitoring an environmental exposure parameter for a user. Examples of measured environmental exposure parameters include, but are not limited to including, ambient temperature, humidity, wind speed, pollen levels, ultra-violet (UV) light exposure, hazardous material exposure, etc. Environmental exposure parameters may be transmitted from environment measurement device 46 to computer system 10 in a transmittable data format, such as XML. Computer system 10 advantageously stores the environmental exposure parameters in health history database 62.

Health data analyzer application 60 analyzes environmental exposure parameters in view of health allowances 68 to determine if the environmental exposure parameters fall within constraints designated in health allowances 68. Health data analyzer application 60 also analyzes the environmental exposure parameters in view of health profile 70 to determine if any warnings are included in association with certain levels of environmental exposure parameters. Moreover, health data analyzer application 60 may also recommend adjustments of health allowances 68 if the environmental health allowances are not allowing a balanced cumulative health.

If the environmental exposure parameters do not fall within designated constraints or are at warning levels, a warning to the user and recommendations may be output from computer system 10. In addition, health data analyzer application 60 may determine control signals for transmission to an environmental control system 56 in order to adjust the environmental exposure parameter that is not acceptable. For example, if a user's environmental allowances indicate a minimum of thirty minutes of exposure to UV light each day in order to reduce chances of suffering from seasonal affect disorder (SAD) and a user has only been exposed to ten minutes of UV light at nightfall, then a control signal for a UV light box to radiate on the user for at least twenty minutes would be determined by health data analyzer application 60 for transmission to the UV light box. In particular, the UV light box may include a sensor that detects when the user is within a particular range of the UV light box and records the amount of exposure. In addition, computer system 10 may be equipped with a light sensor that detects the UV light exposure of the user.

Health data analyzer application 60 may advantageously analyze health history database 62 in view of environmental exposure parameters and bodily health parameters in correlation with a user's geographic location and tasks in order to determine health effecting factors for the user. For example, it may be determined that a particular geographic location includes an allergen that makes the user's heart rate and pulse increase. In another example, health data analyzer application 60 may determine that a particular climate is particularly advantageous for user's health.

In a particular example, financial allowances 67 may include an allowance for environment control device 56, such as an air conditioning system, and a rate at which billing occurs. Health data analyzer application 60 may determine control signals to transmit to the air conditioning system for setting the thermostat of the air conditioning system in order to balance a user's comprehensive health in view of the allowance for air conditioning and health needs of the user, whether for a high temperature or lower temperature.

In another example, health data analyzer application 60 may determine recommended clothing and nourishment for a user based on detected environmental parameters and expected environmental parameters. For example, if a user is planning a backpacking trip in a particular region, health data analyzer application 60 may request access to monitored temperatures and other environmental parameters for the region and recommend specified types of outdoor gear for the user.

Cumulative Exercise

As described in U.S. patent application Ser. No. 09/561, 115, herein incorporated by reference, an electronic exercise monitoring device 48 provides a device for monitoring physical health parameters for a user. Examples of measured physical health parameters include, but are not limited to, distance, speed, elevation, weight, intensity, direction, strokes, cycles, steps climbed, etc. Physical health parameters may be transmitted from exercise monitoring device 48 to computer system 10 in a transmittable data format, such as XML.

Health data analyzer application 60 analyzes physical health parameters in view of health allowances 68 to determine if the physical health parameters fall within constraints designated in health allowances 68. Health data analyzer 60 also analyzes the physical health parameters in view of health profile 70 to determine if any warnings are included in association with certain levels of physical health parameters. Moreover, health data analyzer application 60 may also recommend adjustments of health allowances 68 if the physical health allowances are not allowing a balanced cumulative health.

If the physical health parameters do not fall within designated constraints or are at warning levels, a warning to the user and recommendations may be output from computer system 10. In addition, health data analyzer application 60 may determine control signals for transmission to an exercise machine controller 58 in order to adjust the physical health parameter that is not acceptable. For example, a user's physical health parameter for elevation on a treadmill may include a minimum of 20° incline. If the treadmill is not inclined at least 20° then a recommendation may be made to the user to manually designate an increase in incline. In addition, health data analyzer application 60 may determine a control signal for transmission to the treadmill in order to increase the inclination of the treadmill.

Electronic schedule 66 may include multiple scheduled tasks for a user to exercise utilizing multiple types of exercise machines and free exercise(free exercise includes exercise performed independent of an exercise machine). A scheduled exercise task may include a control program for transmission to the exercise machine controller 58 for controlling an exercise session at a particular type of exercise machine. For example, a scheduled exercise task may include a first control program for controlling a treadmill for twenty minutes and a second control program for controlling a rowing machine for fifteen minutes. In particular, a user may designate an exercise task for scheduling in electronic schedule 66, health data analyzer application 60 may determine exercise tasks according to a user's heath allowances 68, or an exercise task may be received from an alternate decision making system.

Advantageously, an exercise machine includes health measurement monitoring devices, such as health measurement monitoring device 44, that monitor bodily health parameters of a user in correlation with exercise monitoring system 48 that monitors physical health parameters of a user. Health data analyzer application 60 analyzes bodily health parameters and physical health parameters in correlation with health profile 70 to determine calories burned, fat burned, cardiovascular strengthening, muscle strengthening and other exercise related benefits. As previously described, health allowances 68 includes constraints for daily, weekly, and/or monthly calories and fat to be burned. In addition, health allowances 68 includes daily, weekly, and/or monthly cardiovascular and muscular strengthening. Therefore, health data analyzer application 60 is enabled to determine if the constraints are reached or not.

In addition, by the present invention, health data analyzer application 60 is enabled to determine cumulative exercise totals for a user from exercise performed across multiple diverse exercise machines and from free exercise. For example, if a user exercises for thirty minutes on a cycling machine and then lifts weights utilizing weight assistance machines, then cumulative exercise totals for calories burned, fat burned, cardiovascular strengthening, and muscle strengthening may be determined by health data analyzer application 60.

Control Group Health Tracking

Advantageously, the comprehensive health of a control group of people can be tracked at multiple types of health tracking systems. Computer system 10 advantageously transmits comprehensive health data from any of health history database 62, electronic schedule 66, financial allowances 67, health allowances 68, health profile 70, and/or electronic preferences 72 to one of multiple health tracking systems. Examples of health tracking systems that are described herein include employer tracking systems, experimentation tracking systems, and public health tracking systems. In addition, alternate types of tracking systems may be utilized in accordance with the method, system and program of the present invention.

Employer Tracking System

Figure 9:
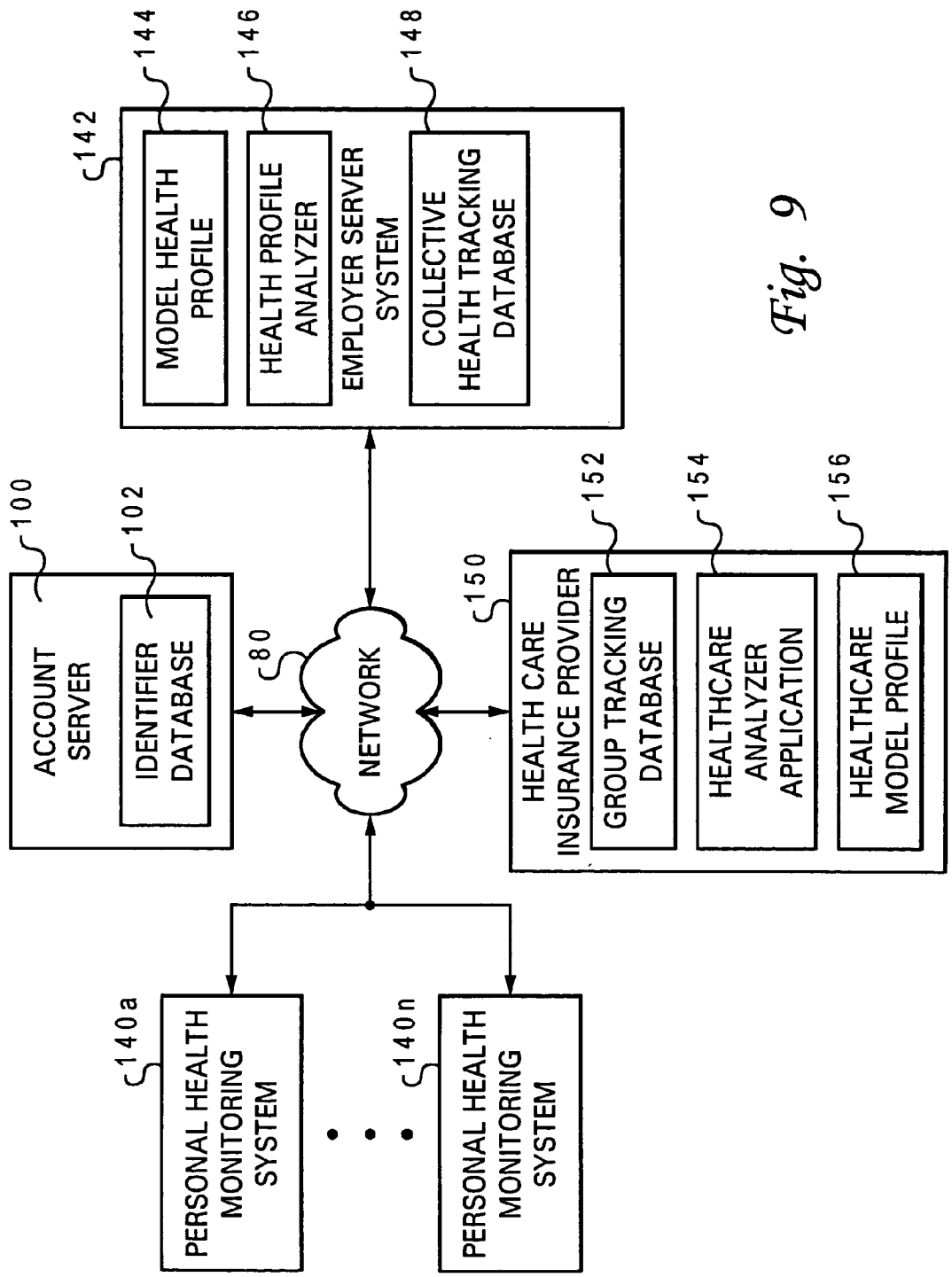
FIG. 9 depicts a block diagram of one embodiment of an employer tracking system in accordance with the method, system and program of the present invention.

With reference now to FIG. 9, there is depicted a block diagram of one embodiment of an employer tracking system in accordance with the method, system and program of the present invention. As illustrated, multiple personal health monitoring systems 140a–140n are connected to network 80 through which comprehensive health data is transmitted to an employer server system 142. Each of personal health monitoring systems 140a–140n and employer server system 142 are accessible through network 80 at a particular network address with an associated universal alphanumeric identifier included in identifier database 102. In particular, employer server system 142 may include multiple server systems or a mainframe in order to provide sufficient processing power.

Employer server system 142 stores comprehensive health data by user at a collective health tracking database 148. A health profile analyzer application 146 at employer server system 142 compares comprehensive health data received with a model health profile 144 to determine whether or not a user is meeting particular health requirements. Users who are not meeting the requirements of model health profile 144 may receive recommendations for adjusting time, financial, and/or health allowances in order to aid the user in meeting the requirements of model health profile 144. In particular, model health profile 144 may include multiple categories of requirements where a user may meet requirements in more than one category. For example, one category of requirements may focus on food intake while another category of requirements focuses on exercise. In addition, model health profile 144 is preferably includes requirements that have been shown to lead to increased productivity, increased overall health, increased longevity, and other results that would be advantageous to an employer and/or to providers of insurance to an employer.

In particular, one category of requirements may focus on employees being free of substances that are prohibited by the employer, such as illegal substances and alcohol. Since many employers are requiring employees to submit to random drug testing, the present system would benefit an employer. Comprehensive health data for each employee may be utilized to determine whether employees are free from prohibited substances.

An employer may utilize analysis of collective health tracking database 148 by health profile analyzer application 146 to determine what actions may be taken by the employer to improve employee comprehensive health and to provide additional benefits to those who meet the requirements of model health profile 144. For example, an employer may determine that a large percentage of employees can not afford to belong to a health club and therefore may provide health club vouchers for employees or provide a gym in the workplace. In another example, an employer may determine that employees eating in the employer's cafeteria are only eating high calorie items because of the taste and therefore may work to adjust the cafeteria menu to include tasty lower calorie options. In yet another example, an employer may determine that those employees who spend four or more hours a week cycling are more productive than those employees who do not cycle and therefore may provide incentives to employees who log four or more hours a week cycling.

In the present embodiment, collective health tracking database 148 may be transmitted from employer server system 142 via network 80 to healthcare insurance provider 150. Collective health tracking database 148 is stored within group tracking database 152 at healthcare insurance provider 150. Healthcare insurance provider 150 includes a healthcare model profile 156 to which collective health tracking database 148 is compared by a health care analyzer application 154.

Healthcare analyzer application 154 determines what percentage of a group of employees are meeting the requirements of healthcare model profile 156, which may or may not include the same requirements as model health profile 142. An employer may receive reduced health care coverage cost if more than a certain percentage of employees are meeting the requirements of model profile 156. Other insurance and employer supporting companies may also provide incentives to employers to encourage balanced comprehensive health among employees. In particular, an employer may also negotiate with an insurance provider for increased benefits or reduced rates depending upon the level of health represented by employees in collective health tracking database 148.

In addition, healthcare analyzer application 154 determines individually which employees are meeting the requirements of healthcare model profile 156. Depending on the portion of requirements of healthcare model profile 156 that an employee is meeting, an employee may receive a voucher or other compensation for pursuing balanced health. In the example of a life insurance company evaluating a user's comprehensive health, the life insurance company may determine a life expectancy for the individual and recommend types of coverage based on the user's life expectancy.

Moreover, healthcare analyzer application 154 may determine whether employees are actually taking medication subsidized by the insurance. In particular, when an employee receives a medication order from a doctor, a copy of that medication order is advantageously sent from the physician accessible server system to healthcare insurance provider 150, such that healthcare insurance provider 150 is enabled to monitor whether or not the user receives the medication and takes the medication properly.

Experimentation Tracking System

Figure 10:
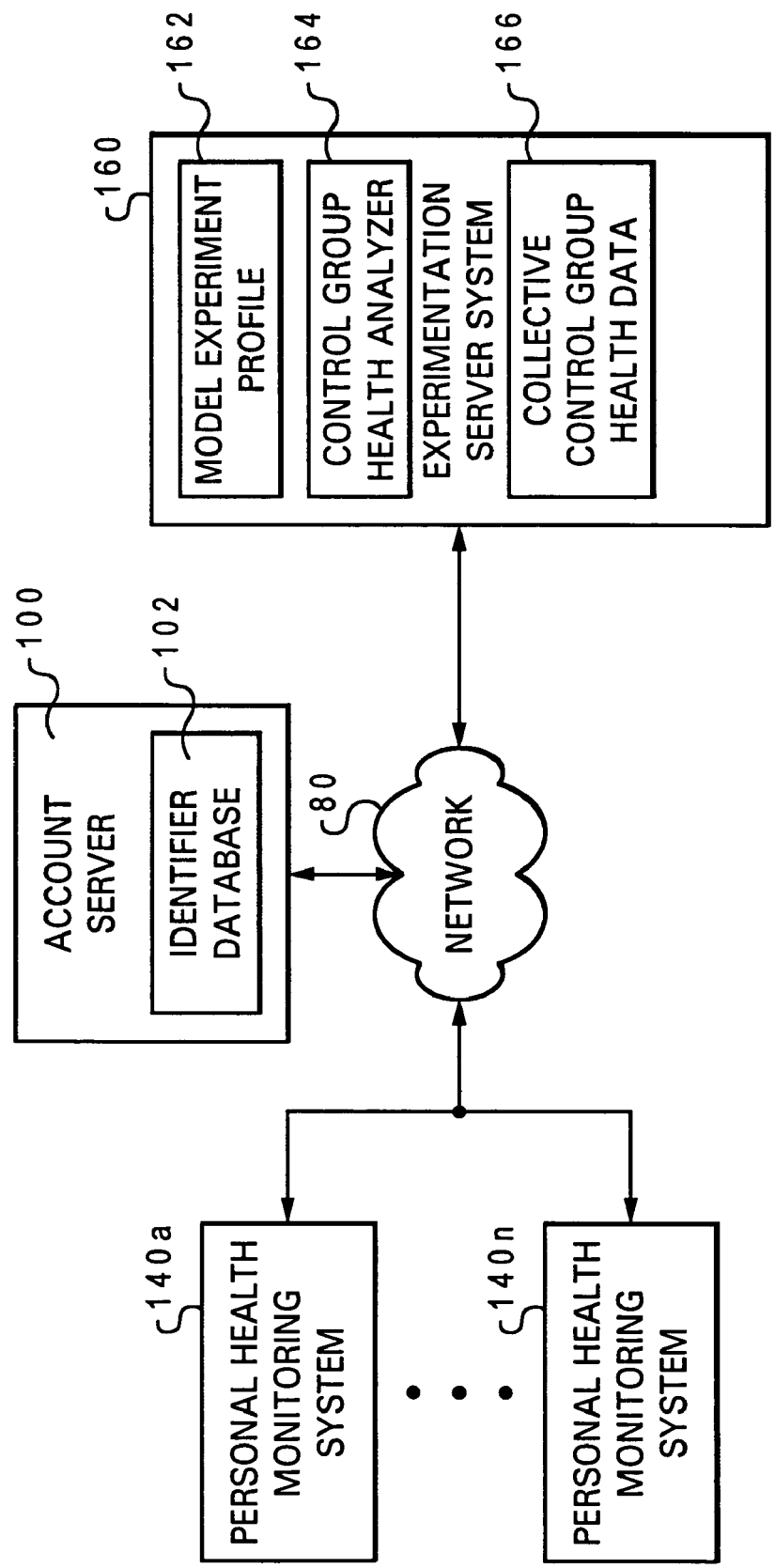
FIG. 10 illustrates a block diagram of one embodiment of an experimentation tracking system in accordance with the method, system and program of the present invention.

Referring now to FIG. 10, there is illustrated a block diagram of one embodiment of an experimentation tracking system in accordance with the method, system and program of the present invention. As illustrated, multiple personal health monitoring systems 140a–140n are connected to network 80 through which comprehensive health data is transmitted to an experimentation server system 160. Each of personal health monitoring systems 140a–140n and experimental server system 160 are accessible through network 80 at a particular network address with an associated universal alphanumeric identifier included in identifier database 102. In particular, experimental server system 160 may include multiple server systems or a mainframe in order to provide sufficient processing power Experimentation server system 160 stores comprehensive health data by user in collective health tracking database 166. Comprehensive health data is preferably received at experimentation server system 160 from control groups of users that are participating in an experiment surrounding a particular area of comprehensive health. Examples of experimentation may include medications, foods, exercise programs, scheduling programs, environmental exposure programs, and others. In particular, experiments performed utilizing the present system advantageously allow a user to function in a normal setting without the need for staying at a testing center. In addition, experiments performed utilizing the present system are advantageous because an experimenter can remotely transmit experimentation changes or updates to a user.

For each experiment there is preferably a model experiment profile 162 that includes health requirements for the user that is participating in the experiment in order to receive compensation. For example, a user participating in a medication experiment may be required to eat at particular times when the experimental medication is being taken. In another example, a user participating in an exercise program experiment may be required to drink a minimum amount of water daily, eat a minimum amount of protein daily, and sleep for a minimum amount of time daily.

Control group health analyzer application 164 compares comprehensive health data received from one of personal health monitoring systems 140a–140n to determine whether or not a control group participant is meeting the requirements of model experiment profile 162. If a user is not meeting the requirements of model experiment profile 162, then warnings and/or recommendations for adjustments to time, financial, and/or health parameters may be determined and transmitted to the appropriate one of personal health monitoring systems 140a–140n.

In addition, control group health analyzer application 164 compares each set of comprehensive health data received for each participant to determine common characteristics of participants. For example, a large percentage of users taking an experimental medication may suffer from a similar side-effect. In another example, in an exercise experimentation, one control group may perform the required exercise with a first set of diet requirements and a second control group may perform the required exercise with a second set of diet requirements, such that the effects of one diet over another in combination with the required exercise may be determined.

Public Health Tracking System

Figure 11:
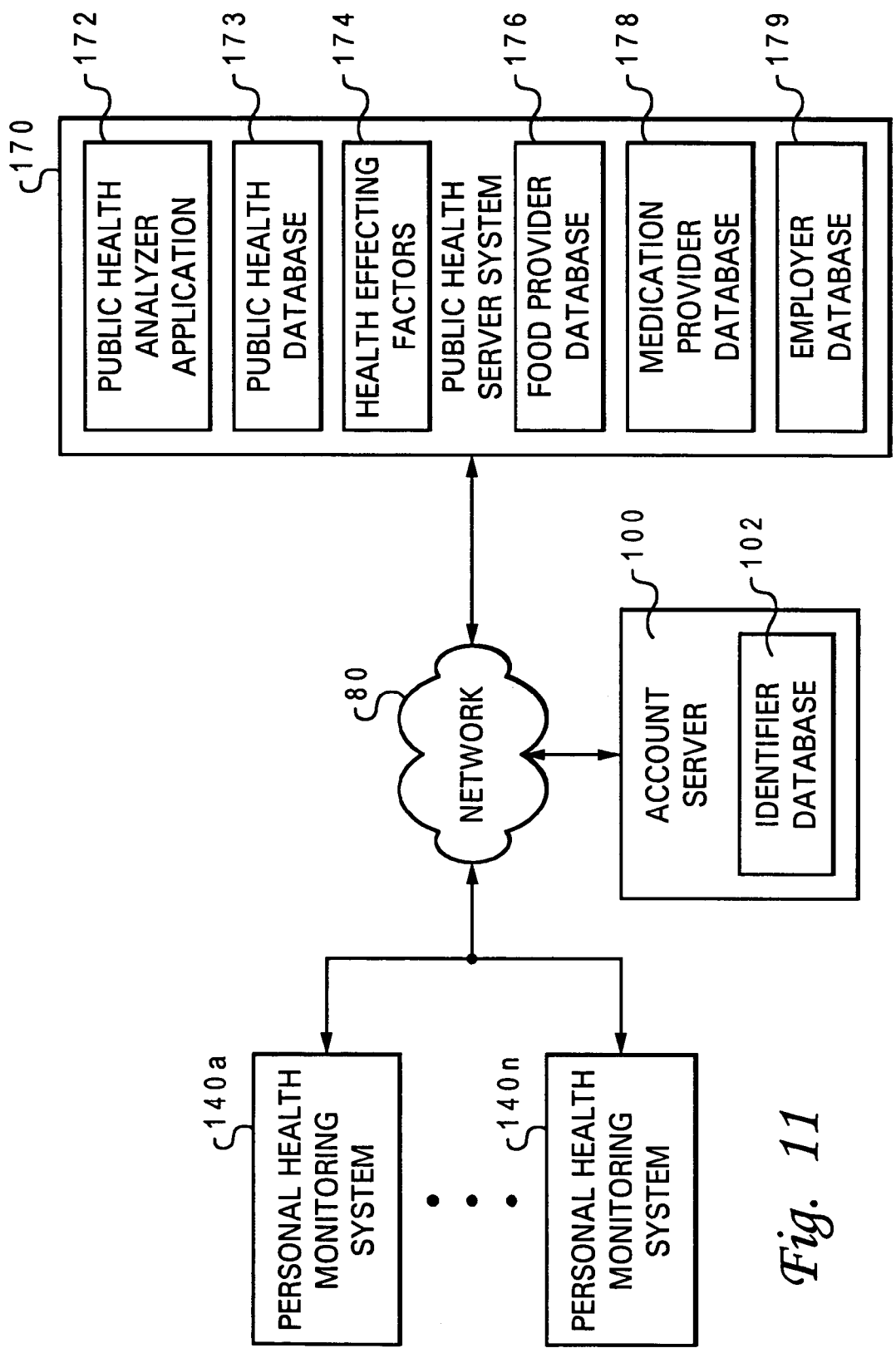
FIG. 11 depicts a block diagram of one embodiment of a public health tracking system in accordance with the method, system and program of the present invention.

With reference now to FIG. 11, there is depicted a block diagram of one embodiment of a public health tracking system in accordance with the method, system and program of the present invention. As illustrated, multiple personal health monitoring systems 140a–140n are connected to network 80 through which comprehensive health data is transmitted to a public health server system 170. Each of personal health monitoring systems 140a–140n and public health server system 170 are accessible through network 80 at a particular network address with an associated universal alphanumeric identifier included in identifier database 102. In particular, public health server system 170 may include multiple server systems or a mainframe in order to provide sufficient processing power.

Public health server system 170 stores comprehensive health data received from personal health monitoring systems 140a–140n in public health database 173. Public health analyzer application 172 analyzes the multiple comprehensive health data entries in public health database 173 to determine health effecting factors of multiple individuals by determining a control group of users that have all been exposed to common grocery foods, restaurants, environments, geographical locations, etc and narrowing down the common exposures to a common health effecting factor. Health effecting factors determined by public health analyzer application 172 are stored in health effecting factors database 179.

In addition, public health analyzer application 172 analyzes the current public health database 173 in view of previously determined health effecting factors in health effecting factors database 173 to determine the presence of each health effecting factor. For example, if a health effecting factor in a particular region is determined, then each entry to public health database 173 where the individual has been in the particular region is analyzed to determine if the health effecting factor continues to affect individuals in the particular region.

Moreover, health effecting factors database 173 include health effecting factors that need to be tested for, but have not necessarily been shown to effect health. For example, a health effecting factor may filter consumers of a particular brand of fruits that are sprayed with a particular pesticide so that any effects of the pesticide may be traced. In another example, a health effecting factor may filter consumers of a particular brand of fruits that are genetically engineered so that any effects of the genetically engineered fruit are traced.

In determining health effecting factors, the responsible party for the health effecting factor is preferably traced if applicable. For example, chemical exposure or food poisoning typically have a responsible party. By the present invention, the comprehensive health data received for each user preferably includes health history database 62 that further provides listings for the grocery store that the user purchased products from, the restaurant that the user ate at, the gym that the user exercised at, the location where the user worked, etc.

Public health server system 170 advantageously includes multiple databases that include information about food providers, medication providers and employers. In particular, food provider database 176 can be searched to determine where a grocery store received each item inventoried by the grocer and can be searched to determine where a restaurant received each food item. Medication database 178 can be searched to determine the manufacturer of any prescription medication, over-the-counter medication, vitamin, or nutritional supplement. In addition, any expected side-effects to medications are preferably available in medication database 178. Employer database 179 can be searched to determine the responsible owner for any business and the facilities provided by the responsible owner.

In addition to searching databases, public health officials may be dispatched to determine the source of a health effecting factor. For example, if it is determined that users are reacting from food poisoning after eating at a particular restaurant, but there is not one particular food item that is causing the illness, a health inspector may be issued to inspect the particular restaurant.

Advantageously, the present public health server system may be utilized by the Food and Drug Administration (FDA) and others to monitor the affects of foods and medications on the public and provide warnings to the public when detrimental health effects are discovered in a food or drug product. In addition, the Environmental Protection Agency (EPA) would benefit from monitoring where public health is being effected from environmental pollution and providing warnings to the public when detrimental environmental areas are discovered. Moreover, the present embodiment would be advantageous for a public heath inspector in determining buildings that may be causing sickness in employees and possible causes, such as molds.

In addition, public health analyzer application 172 may analyze common health problems by groups of people planning on attending a particular event. For example, public health analyzer application 172 may determine that over 20% of the people who have scheduled to attend a particular ball game on Saturday are diabetic. Therefore, public health analyzer application 172 would recommend that a particular amount of insulin and glucose be available to medics at the ball game in order to be prepared for the number of diabetics planning to attend the ball game.

Figure 12:
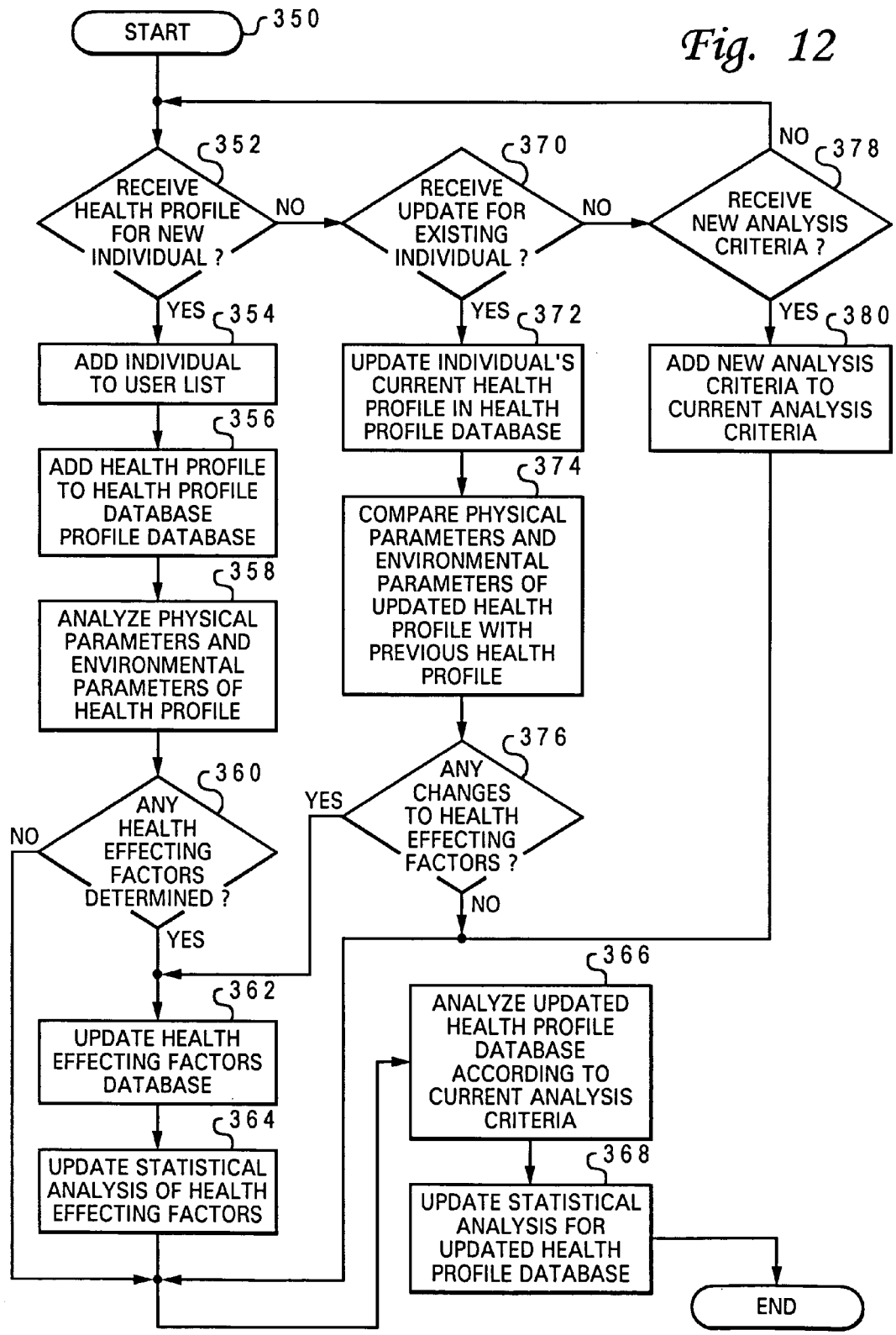
FIG. 12 illustrates a high level logic flowchart of a process and program for tracking the comprehensive health of a control group in accordance with the present invention.

Referring now to FIG. 12, there is illustrated a high level logic flowchart of a process and program for tracking the comprehensive health of a control group in accordance with the present invention. As depicted, the process starts at block 350 and thereafter proceeds to block 352. Block 352 illustrates a determination as to whether or not a health profile for a new individual is received. If a health profile for a new individual is not received, then the process passes to block 370. If a health profile for a new individual is received, then the process passes to block 354.

Block 354 depicts adding the individual to a user list. Next, block 356 illustrates adding the user's health profile and/or health history database to the health profile database. Next, block 358 depicts analyzing the physical parameters and environmental parameters of the health profile and/or health history database to determine health effecting factors. Thereafter, block 360 illustrates a determination as to whether or not any health effecting factors are determined. If health effecting factors are not determined, then the process passes to block 366. If health effecting factors are determined then the process passes to block 362.

Block 362 illustrates updating the health effecting factors database. Next, block 364 depicts updating the statistical analysis for the determined health effecting factors for the new individual. Thereafter, block 366 illustrates analyzing the updated health profile database according to current analysis criteria, including health effecting factors in the health effecting factors database. Next, block 368 depicts updating the statistical analysis for the updated health profile database; and the process ends.

Block 370 depicts a determination as to whether or not an update for an existing individual is received. If an update for an existing individual is not received, then the process passes to block 378. If an update for an existing individual is received, then the process passes to block 372.

Block 372 illustrates updating the individual's current health profile in the health profile database. Next, block 374 depicts comparing the physical parameters and environmental parameters of the updated health profile with the previous health profile. Thereafter, block 376 illustrates a determination as to whether or not there are any changes to the health effecting factors for the individual. If there are not any changes to the health effecting factors, then the process passes to block 366. If there are changes to the health effecting factors, then the process passes to block 362.

Block 378 depicts a determination as to whether or not new analysis criteria is received. If new analysis criteria is not received, then the process passes to block 352. If new analysis criteria is received, then the process passes to block 380. Block 380 illustrates adding the new analysis criteria to the current analysis criteria; and the process passes to block 366.

It is important to note that, although the present invention has been described in the context of a fully functional computer system, those skilled in the art will appreciate that the mechanisms of the present invention are capable of being distributed as a program product in a variety of forms, and that the present invention applies equally regardless of the particular type of signal-bearing media utilized to actually carry out the distribution. Examples of signal-bearing media include, but are not limited to, recordable-type media such as floppy disks or CD-ROMs and transmission-type media such as analogue or digital communications links.

While the invention has been particularly shown and described with reference to a preferred embodiment, it will be understood by those skilled in the art that various changes in form and detail may be made therein without departing from the spirit and scope of the invention.

What is claimed is:

1. A method for prioritizing actions in order to balance the comprehensive health of a user, said method comprising the steps of:

automatically monitoring current health parameters for a particular user at a personal health monitoring system, wherein said current health parameters includes a plurality of monitored physical parameters and a plurality of monitored environmental parameters;

receiving a plurality of actions for selection by said particular user at said personal health monitoring system;

prioritizing said plurality of actions according to said current health parameters and designated allowances for said particular user at said personal health monitoring system;

presenting the prioritized plurality of actions for selection by said particular user, such that said personal health monitoring system aids said particular user in selecting from among said plurality of actions in order to balance the comprehensive health of said particular user; and determining a priority level at which sufficient allowances are available for each of said plurality of actions in view of said designated allowances, wherein said designated allowances includes at least one type of allowance from among time allowances, financial allowances, and health allowances.

2. The method for prioritizing actions in order to balance the comprehensive health of a user according to claim 1, said step of monitoring current health parameters for a particular user at said personal health monitoring system further comprising the step of:

monitoring medication intake by said particular user.

3. The method for prioritizing actions in order to balance the comprehensive health of a user according to claim 1, said step of monitoring current health parameters for a particular user at said personal health monitoring system further comprising the step of:

monitoring food and liquid intake by said particular user.

4. The method for prioritizing actions in order to balance the comprehensive health of a user according to claim 1, said step of monitoring current health parameters for a particular user at said personal health monitoring system further comprising the step of:

monitoring environmental exposure of said particular user.

5. The method for prioritizing actions in order to balance the comprehensive health of a user according to claim 1, said step of monitoring current health parameters for a particular user at said personal health monitoring system further comprising the step of:

monitoring exercise performed by said particular user.

6. The method for prioritizing actions in order to balance the comprehensive health of a user according to claim 1, said step of monitoring current health parameters for a particular user at said personal health monitoring system further comprising the step of:

monitoring bodily health indicators for said particular user.

7. The method for prioritizing actions in order to balance the comprehensive health of a user according to claim 1, said step of receiving a plurality of actions for selection by said particular user at said personal health monitoring system, further comprising the step of:

receiving a plurality of selectable medication orders at said personal health monitoring system from a physician accessible server system.

8. The method for prioritizing actions in order to balance the comprehensive health of a user according to claim 1, said step of receiving a plurality of actions for selection by said particular user at said personal health monitoring system, further comprising the step of:

receiving a plurality of selectable food menu items at said personal health monitoring system from a restaurant menu server.

9. The method for prioritizing actions in order to balance the comprehensive health of a user according to claim 1, said step of receiving a plurality of actions for selection by said particular user at said personal health monitoring system, further comprising the step of:

receiving a plurality of selectable electronic recipes at said personal health monitoring system from an electronic recipe server.

10. The method for prioritizing actions in order to balance the comprehensive health of a user according to claim 1, said step of prioritizing said plurality of actions, according to said current health parameters and designated allowances for said particular user at said personal health monitoring system, further comprising the step of:

determining whether each of said plurality of selectable actions are allowed according to a plurality of conditional requirements for allowance of said plurality of selectable actions.

11. The method for prioritizing actions in order to balance the comprehensive health of a user according to claim 1, said method further comprising the steps of:

transmitting said plurality of actions, said health profile and said designated allowances to an alternate decision making system; and receiving a prioritization of said plurality of actions from said alternate decision making system at said personal health monitoring system.

12. The method for prioritizing actions in order to balance the comprehensive health of a user according to claim 1, said method further comprising the step of:

filtering said plurality of actions according to electronic preferences designated by said particular user at said personal health monitoring system.

13. A system for prioritizing actions in order to balance the comprehensive health of a user, said system comprising:

means for automatically monitoring current health parameters for a particular user at a personal health monitoring system, wherein said current health parameters includes a plurality of monitored physical parameters and a plurality of monitored environmental parameters;

means for receiving a plurality of actions for selection by said particular user at said personal health monitoring system;

means for prioritizing said plurality of actions according to said current health parameters and designated allowances for said particular user at said personal health monitoring systems means for presenting the prioritized plurality of actions for selection by said particular user, such that said personal health monitoring system aids said particular user in selecting from among said plurality of actions in order to balance the comprehensive health of said particular user; and means for determining a priority level at which sufficient allowances are available for each of said plurality of actions in view of said designated allowances, wherein said designated allowances includes at least one type of allowance from among time allowances, financial allowances, and health allowances.

14. The system for prioritizing actions in order to balance the comprehensive health of a user according to claim 13, said means for monitoring current health parameters for a particular user at said personal health monitoring system further comprising:

means for monitoring medication intake by said particular user.

15. The system for prioritizing actions in order to balance the comprehensive health of a user according to claim 13, said means for monitoring current health parameters for a particular user at said personal health monitoring system further comprising:

means for monitoring food and liquid intake by said particular user.

16. The system for prioritizing actions in order to balance the comprehensive health of a user according to claim 13, said means for monitoring current health parameters for a particular user at said personal health monitoring system further comprising:

means for monitoring environmental exposure of said particular user.

17. The system for prioritizing actions in order to balance the comprehensive health of a user according to claim 13, said means for monitoring current health parameters for a particular user at said personal health monitoring system further comprising:

means for monitoring exercise performed by said particular user.

18. The system for prioritizing actions in order to balance the comprehensive health of a user according to claim 13, said means for monitoring current health parameters for a particular user at said personal health monitoring system further comprising:

means for monitoring bodily health indicators for said particular user.

19. The system for prioritizing actions in order to balance the comprehensive health of a user according to claim 13, said means for receiving a plurality of actions for selection by said particular user at said personal health monitoring system, further comprising:

means for receiving a plurality of selectable medication orders at said personal health monitoring system from a physician accessible server system.

20. The system for prioritizing actions in order to balance the comprehensive health of a user according to claim 13, said means for receiving a plurality of actions for selection by said particular user at said personal health monitoring system, further comprising:
means for receiving a plurality of selectable food menu items at said personal health monitoring system from a restaurant menu server.

21. The system for prioritizing actions in order to balance the comprehensive health of a user according to claim 13, said means for receiving a plurality of actions for selection by said particular user at said personal health monitoring system, further comprising:
means for receiving a plurality of selectable electronic recipes at said personal health monitoring system from an electronic recipe server.

22. The system for prioritizing actions in order to balance the comprehensive health of a user according to claim 13, said means for prioritizing said plurality of actions according to said current health parameters and designated allowances for said particular user at said personal health monitoring system, further comprising:
means for determining a priority level at which sufficient allowances are available for each of said plurality of actions in view of said designated allowances, wherein said designated allowances includes at least one type of allowance from among time allowances, financial allowances, and health allowances.

23. The system for prioritizing actions in order to balance the comprehensive health of a user according to claim 13, said means for prioritizing said plurality of actions according to said current health parameters and designated allowances for said particular user at said personal health monitoring system, further comprising:
means for determining whether each of said plurality of selectable actions are allowed according to a plurality of conditional requirements for allowance of said plurality of selectable actions.

24. The system for prioritizing actions in order to balance the comprehensive health of a user according to claim 13, said system further comprising:
means for transmitting said plurality of actions, said health profile and said designated allowances to an alternate decision making system; and
means for receiving a prioritization of said plurality of actions from said alternate decision making system at said personal health monitoring system.

25. The system for prioritizing actions in order to balance the comprehensive health of a user according to claim 13, said system further comprising:
means for filtering said plurality of actions according to electronic preferences designated by said particular use at said personal health monitoring system.

26. A program for prioritizing actions in order to balance the comprehensive health of a user, residing on a computer usable medium having computer readable program code means, said program comprising:
means for automatically monitoring current health parameters for a particular user at a personal health monitoring system, wherein said current health parameters includes a plurality of monitored physical parameters and a plurality of monitored environmental parameters;
means for receiving a plurality of actions for selection by said particular user at said personal health monitoring system;
means for prioritizing said plurality of actions according to said current health parameters and designated allowances for said particular user at said personal health monitoring system;
means for presenting the prioritized plurality of actions for selection by said particular user, such that said personal health monitoring system aids said particular user in selecting from among said plurality of actions in order to balance the comprehensive health of said particular user; and
means for determining a priority level at which sufficient allowances are available for each of said plurality of actions in view of said designated allowances, wherein said designated allowances includes at least one type of allowance from among time allowances, financial allowances, and health allowances.

27. The program for prioritizing actions in order to balance the comprehensive health of a user according to claim 26, said program further comprising:
means for monitoring medication intake by said particular user.

28. The program for prioritizing actions in order to balance the comprehensive health of a user according to claim 26, said program further comprising:
means for monitoring food and liquid intake by said particular user.

29. The program for prioritizing actions in order to balance the comprehensive health of a user according to claim 26, said program further comprising:
means for monitoring environmental exposure of said particular user.

30. The program for prioritizing actions in order to balance the comprehensive health of a user according to claim 26, said program further comprising:
means for monitoring exercise performed by said particular user.

31. The program for prioritizing actions in order to balance the comprehensive health of a user according to claim 26, said program further comprising:
means for monitoring bodily health indicators for said particular user.

32. The program for prioritizing actions in order to balance the comprehensive health of a user according to claim 26, said program further comprising:
means for receiving a plurality of selectable medication orders at said personal health monitoring system from a physician accessible server system.

33. The program for prioritizing actions in order to balance the comprehensive health of a user according to claim 26, said program further comprising:
means for receiving a plurality of selectable food menu items at said personal health monitoring system from a restaurant menu server.

34. The program for prioritizing actions in order to balance the comprehensive health of a user according to claim 26, said program further comprising:
means for receiving a plurality of selectable electronic recipes at said personal health monitoring system from an electronic recipe server.

35. The program for prioritizing actions in order to balance a comprehensive health of a user according to claim 26, said program further comprising:
means for determining a priority level at which sufficient allowances are available for each of said plurality of actions in view of said designated allowances, wherein said designated allowances includes at least one type of allowance from among time allowances, financial allowances, and health allowances.

36. The program for prioritizing actions in order to balance the comprehensive health of a user according to claim 26, said program further comprising:
   means for determining whether each of said plurality of selectable actions are allowed according to a plurality of conditional requirements for allowance of said plurality of selectable actions.

37. The program for prioritizing actions in order to balance the comprehensive health of a user according to claim 26, said program further comprising:
   means for transmitting said plurality of actions, said health profile and said designated allowances to an alternate decision making system; and
   means for receiving a prioritization of said plurality of actions from said alternate decision making system at said personal health monitoring system.

38. The program for prioritizing actions in order to balance the comprehensive health of a user according to claim 26, said program further comprising:
   means for filtering said plurality of actions according to electronic preferences designated by said particular use at said personal health monitoring system.

39. A method for scheduling tasks in order to balance the comprehensive health of a user, said method comprising the steps of:
   monitoring current health parameters for a particular user at a personal health monitoring system, wherein said current health parameters includes a plurality of monitored physical parameters and a plurality of monitored environmental parameters;
   receiving a plurality of tasks for said particular user for scheduling at said personal health monitoring system; and
   selecting suitable times for scheduling said plurality of tasks in view of said current health parameters and designated allowances for said particular user at said personal health monitoring system, such that said personal health monitoring system aids said particular user in scheduling tasks in order to balance the comprehensive health of said particular user.

40. The method for scheduling tasks in order to balance the comprehensive health of a user according to claim 39, said method further comprising the steps of:
   receiving said plurality of tasks with a priority assigned to each of said plurality of tasks; and
   selecting suitable times for scheduling said plurality of tasks according to said priority assigned to each of said plurality of tasks and a priority assigned to each task already scheduled.

41. The method for scheduling tasks in order to balance the comprehensive health of a user according to claim 39, said step of receiving a plurality of tasks for said particular user for scheduling at said personal health monitoring system, further comprising the step of:
   receiving said plurality of tasks for said particular user from an alternate decision making system.

42. The method for scheduling tasks in order to balance the comprehensive health of a user according to claim 39, said step of receiving a plurality of tasks for said particular user for scheduling at said personal health monitoring system, further comprising the step of:
   internally determining said plurality of tasks for said particular user at said personal health monitoring system according to said current health parameters and said designated allowances.

43. The method for scheduling tasks in order to balance the comprehensive health of a user according to claim 39, said step of receiving a plurality of tasks for said particular user for scheduling at said personal health monitoring system, further comprising the step of:
   receiving said plurality of tasks from said particular user via an input interface coupled to said personal health monitoring system.

44. The method for scheduling tasks in order to balance the comprehensive health of a user according to claim 39, said step of selecting suitable times for scheduling said plurality of tasks in view of said current health parameters and designated allowances for said particular user, further comprising the steps of:
   determining whether a particular task from among said plurality of tasks is schedulable; and
   prompting said particular user to determine whether or not to schedule said particular task, in response to determining that said particular task is not schedulable.

45. The method for scheduling tasks in order to balance the comprehensive health of a user according to claim 39, said method further comprising the step of:
   determining whether each of said plurality of tasks is allowable according to designated conditional time requirements at said personal health monitoring system.

46. The method for scheduling tasks in order to balance the comprehensive health of a user according to claim 39, said method further comprising the step of:
   scheduling tasks in an electronic schedule according to time allowances designated by said particular user.

47. The method for scheduling tasks in order to balance the comprehensive health of a user according to claim 46, said method further comprising the step of:
   indicating whether a scheduled task requires verification of performance.

48. A system for scheduling tasks in order to balance the comprehensive health of a user, said system comprising:
   means for monitoring current health parameters for a particular user at a personal health monitoring system, wherein said current health parameters includes a plurality of monitored physical parameters and a plurality of monitored environmental parameters;
   means for receiving a plurality of tasks for said particular user for scheduling, at said personal health monitoring system; and
   means for selecting suitable times for scheduling said plurality of tasks in view of said current health parameters and designated allowances for said particular user at said personal health monitoring system, such that said personal health monitoring system aids said particular user in scheduling tasks in order to balance a comprehensive health of said particular user.

49. The system for scheduling tasks in order to balance the comprehensive health of a user according to claim 48, said system further comprising:
   means for receiving said plurality of tasks with a priority assigned to each of said plurality of tasks; and
   means for selecting suitable times for scheduling said plurality of tasks according to said priority assigned to each of said plurality of tasks and a priority assigned to each task already scheduled.

50. The system for scheduling tasks in order to balance the comprehensive health of a user according to claim 48, said means for receiving a plurality of tasks for said particular user for scheduling at said personal health monitoring system, further comprising:
    means for receiving said plurality of tasks for said particular user from an alternate decision making system.

51. The system for scheduling tasks in order to balance the comprehensive health of a user according to claim 48, said means for receiving a plurality of tasks for said particular user for scheduling at said personal health monitoring system, further comprising:
    means for internally determining said plurality of tasks for said particular user at said personal health monitoring system according to said current health parameters and said designated allowances.

52. The system for scheduling tasks in order to balance the comprehensive health of a user according to claim 48, said means for receiving a plurality of tasks for said particular user for scheduling at said personal health monitoring system, further comprising:
    means for receiving said plurality of tasks from said particular user via an input interface coupled to said personal health monitoring system.

53. The system for scheduling tasks in order to balance the comprehensive health of a user according to claim 48, said means for selecting suitable times for scheduling said plurality of tasks in view of said current health parameters and designated allowances for said particular user, further comprising:
    means for determining whether a particular task from among said plurality of tasks is schedulable; and
    means for prompting said particular user to determine whether or not to schedule said particular task, in response to determining that said particular task is not schedulable.

54. The system for scheduling tasks in order to balance the comprehensive health of a user according to claim 48, said system further comprising:
    means for determining whether each of said plurality of tasks is allowable according to designated conditional time requirements at said personal health monitoring system.

55. The system for scheduling tasks in order to balance the comprehensive health of a user according to claim 48, said system further comprising:
    means for scheduling tasks in an electronic schedule according to time allowances designated by said particular user.

56. The system for scheduling tasks in order to balance the comprehensive health of a user according to claim 55, said system further comprising:
    means for indicating whether a scheduled task requires verification of performance.

57. A program for scheduling tasks in order to balance the comprehensive health of a user, residing on a computer usable medium having computer readable program code means, said program comprising:
    means for monitoring current health parameters for a particular user at a personal health monitoring system, wherein said current health parameters includes a plurality of monitored physical parameters and a plurality of monitored environmental parameters;
    means for receiving a plurality of tasks for said particular user for scheduling at said personal health monitoring system; and
    means for selecting suitable times for scheduling said plurality of tasks in view of said current health parameters and designated allowances for said particular user at said personal health monitoring system, such that said personal health monitoring system aids said particular user in scheduling tasks in order to balance the comprehensive health of said particular user.

58. The program for scheduling tasks in order to balance the comprehensive health of a user according to claim 57, said program further comprising:
    means for receiving said plurality of tasks with a priority assigned to each of said plurality of tasks; and
    means for selecting suitable times for scheduling said plurality of tasks according to said priority assigned to each of said plurality of tasks and a priority assigned to each task already scheduled.

59. The program for scheduling tasks in order to balance the comprehensive health of a user according to claim 57, said program further comprising:
    means for receiving said plurality of tasks for said particular user from an alternate decision making system.

60. The program for scheduling tasks in order to balance the comprehensive health of a user according to claim 57, said program further comprising:
    means for internally determining said plurality of tasks for said particular user at said personal health monitoring system according to said current health parameters and said designated allowances.

61. The program for scheduling tasks in order to balance the comprehensive health of a user according to claim 57, said program further comprising:
    means for receiving said plurality of tasks from said particular user via an input interface coupled to said personal health monitoring system.

62. The program for scheduling tasks in order to balance the comprehensive health of a user according to claim 57, said program further comprising:
    means for determining whether a particular task from among said plurality of tasks is schedulable; and
    means for prompting said particular user to determine whether or not to schedule said particular task, in response to determining that said particular task is not schedulable.

63. The program for scheduling tasks in order to balance the comprehensive health of a user according to claim 57, said program further comprising:
    means for determining whether each of said plurality of tasks is allowable according to designated conditional time requirements at said personal health monitoring system.

64. The program for scheduling tasks in order to balance the comprehensive health of a user according to claim 57, said program further comprising:
    means for scheduling tasks in an electronic schedule according to time allowances designated by said particular user.

65. The program for scheduling tasks in order to balance the comprehensive health of a user according to claim 64, said program further comprising:
    means for indicating whether a scheduled task requires verification of performance.

* * * * *